(12) United States Patent
Piccolo-Wignall et al.

(10) Patent No.: US 10,966,887 B2
(45) Date of Patent: Apr. 6, 2021

(54) REMOVABLE CARTRIDGES FOR A SPINE BOARD

(71) Applicant: Rx 1186, LLC, Fairfield, CA (US)

(72) Inventors: John Piccolo-Wignall, Fairfield, CA (US); Douglas C. Fritz, Napa, CA (US); James R. Osborn, Richmond, CA (US)

(73) Assignee: RX 1186, LLC, Fairfield, CA (US)

( * ) Notice: Subject to any disclaimer, the term of this patent is extended or adjusted under 35 U.S.C. 154(b) by 744 days.

(21) Appl. No.: 15/793,051

(22) Filed: Oct. 25, 2017

(65) Prior Publication Data

US 2018/0042792 A1 Feb. 15, 2018

Related U.S. Application Data

(63) Continuation of application No. 15/707,435, filed on Sep. 18, 2017, which is a continuation-in-part of application No. 14/792,981, filed on Jul. 7, 2015, now Pat. No. 9,763,838.

(60) Provisional application No. 62/022,308, filed on Jul. 9, 2014.

(51) Int. Cl.
| | |
|---|---|
| *A61G 1/044* | (2006.01) |
| *A61F 5/37* | (2006.01) |
| *A61G 7/10* | (2006.01) |
| *A61G 1/04* | (2006.01) |

(Continued)

(52) U.S. Cl.
CPC .............. *A61G 1/044* (2013.01); *A61F 5/055* (2013.01); *A61F 5/3761* (2013.01); *A61G 1/04* (2013.01); *A61G 7/1084* (2013.01); *A61G 1/048* (2013.01)

(58) Field of Classification Search
CPC .... A61F 5/3761; A61F 5/3769; A61F 5/3776; A61F 5/055; A61F 5/05; A61F 5/05883; A61G 1/04; A61G 1/044; A61G 1/048; A61G 7/1084; A47C 31/08; A47C 7/22;
(Continued)

(56) References Cited

U.S. PATENT DOCUMENTS

| | | |
|---|---|---|
| 3,449,776 A | 6/1969 | Brock |
| 4,267,830 A | 5/1981 | Vick |
| 4,473,912 A | 10/1984 | Scheldel et al. |

(Continued)

FOREIGN PATENT DOCUMENTS

WO 86/07253 A1 12/1986

OTHER PUBLICATIONS

European Office Action dated Feb. 6, 2019 for European Application No. 18192675.9 filed Sep. 5, 2018, 6 pages.
(Continued)

*Primary Examiner* — Kari K Rodriquez
(74) *Attorney, Agent, or Firm* — Leanne Taveggia Farrell; Westman, Champlin & Koehler, P.A.

(57) ABSTRACT

A removable cartridge configured to be inserted into a receiving channel. The cartridge includes an elongated body having a leading end, a trailing end, a top surface and a bottom surface. A button protrudes from the top surface of the elongated body and is positioned proximate the trailing end of the elongated body. When the cartridge is being inserted into the receiving channel, the button is compressed. After the cartridge is inserted into the receiving channel, the button releases into an opening that intersects with the receiving channel so as to lock the cartridge in the channel.

15 Claims, 25 Drawing Sheets

(51) Int. Cl.
*A61F 5/055* (2006.01)
*A61G 1/048* (2006.01)

(58) Field of Classification Search
CPC .............. A47C 7/0213; A62B 35/0006; A62B 35/0018; A62B 35/0031; A62B 35/0062
USPC ..................................... 128/870; 5/625, 628
See application file for complete search history.

(56) References Cited

U.S. PATENT DOCUMENTS

| | | | |
|---|---|---|---|
| 4,506,664 | A | 3/1985 | Brault |
| 4,534,075 | A | 8/1985 | Schnitzler |
| 4,736,474 | A | 4/1988 | Moran et al. |
| 4,895,173 | A | 1/1990 | Brault et al. |
| 4,945,583 | A | 8/1990 | Schnitzler |
| 5,121,514 | A | 6/1992 | Rosane |
| 5,121,576 | A | 6/1992 | Koledin |
| 5,121,756 | A | 6/1992 | Koledin |
| 5,334,133 | A * | 8/1994 | Carroll .................... A61F 5/055 128/870 |
| 5,433,741 | A | 7/1995 | Truglio |
| 5,839,137 | A | 11/1998 | Butler et al. |
| 5,865,780 | A | 2/1999 | Tuite |
| 5,944,016 | A * | 8/1999 | Ferko, III ........... A61F 5/05883 128/869 |
| 6,055,988 | A | 5/2000 | Perisho |
| D479,878 | S | 9/2003 | Phillips et al. |
| D511,835 | S | 11/2005 | Holland |
| 6,966,321 | B2 | 11/2005 | Hess |
| 7,055,199 | B2 | 6/2006 | Thompson |
| 7,120,954 | B2 | 10/2006 | Traut et al. |
| 7,165,278 | B2 | 1/2007 | Tomcany et al. |
| 7,360,264 | B2 | 4/2008 | Tomcany |
| 7,426,761 | B2 | 9/2008 | Tomcany et al. |
| 7,437,789 | B2 | 10/2008 | Thompson |
| 7,520,009 | B1 * | 4/2009 | Heck ........................ A61G 1/01 128/870 |
| 2008/0086817 | A1 | 4/2008 | Zucker et al. |
| 2009/0173354 | A1 | 7/2009 | Gold |
| 2011/0185504 | A1 | 8/2011 | Kenalty et al. |
| 2012/0102650 | A1 * | 5/2012 | McGlynn ............... A61G 1/048 5/627 |
| 2014/0068865 | A1 | 3/2014 | Heck |

OTHER PUBLICATIONS

European Search Report dated Feb. 20, 2019 for European Application No. 18192675.9 filed Sep. 5, 2018, 7 pages.
Canadian Office Action dated Nov. 15, 2019 for Canadian Application No. 2,992,476, 3 pages.
Canadian Office Action dated Feb. 13, 2019 for Canadian Application No. 2,991,476, 6 pages.
European Office Action dated Apr. 10, 2018 for European Application No. 15 747 863.7 filed Jan. 24, 2017, 4 pages.
Invitation to Pay Additional Fees dated Nov. 6, 2015 for International Application No. PCT/US2015/039481 filed Jul. 8, 2015, 5 pages.
International Search Report and Written Opinion dated Jan. 28, 2016 for International Application No. PCT/US2015/039481 filed Jul. 8, 2015, 15 pages.
Office Action dated Aug. 10, 2016 for U.S. Appl. No. 14/792,981, filed Jul. 7, 2015, 7 pages.
Final Office Action dated Mar. 9, 2017 for U.S. Appl. No. 14/792,981, filed Jul. 7, 2015, 6 pages.
Canadian Office Action dated Jun. 13, 2019 for Canadian Application No. 2,992,072 filed Jan. 17, 2018, 3 pages.

* cited by examiner

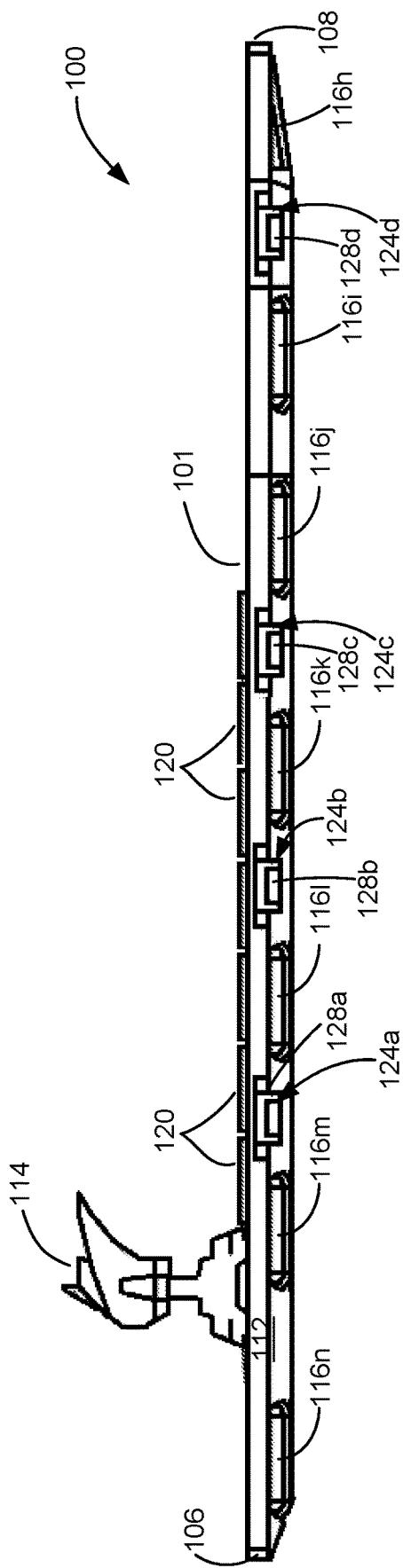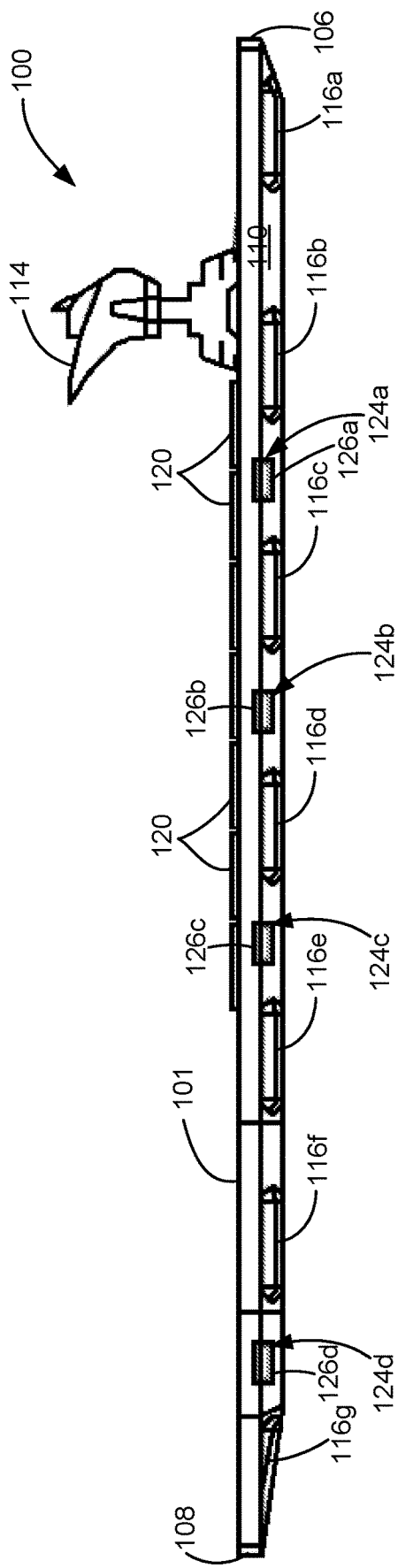

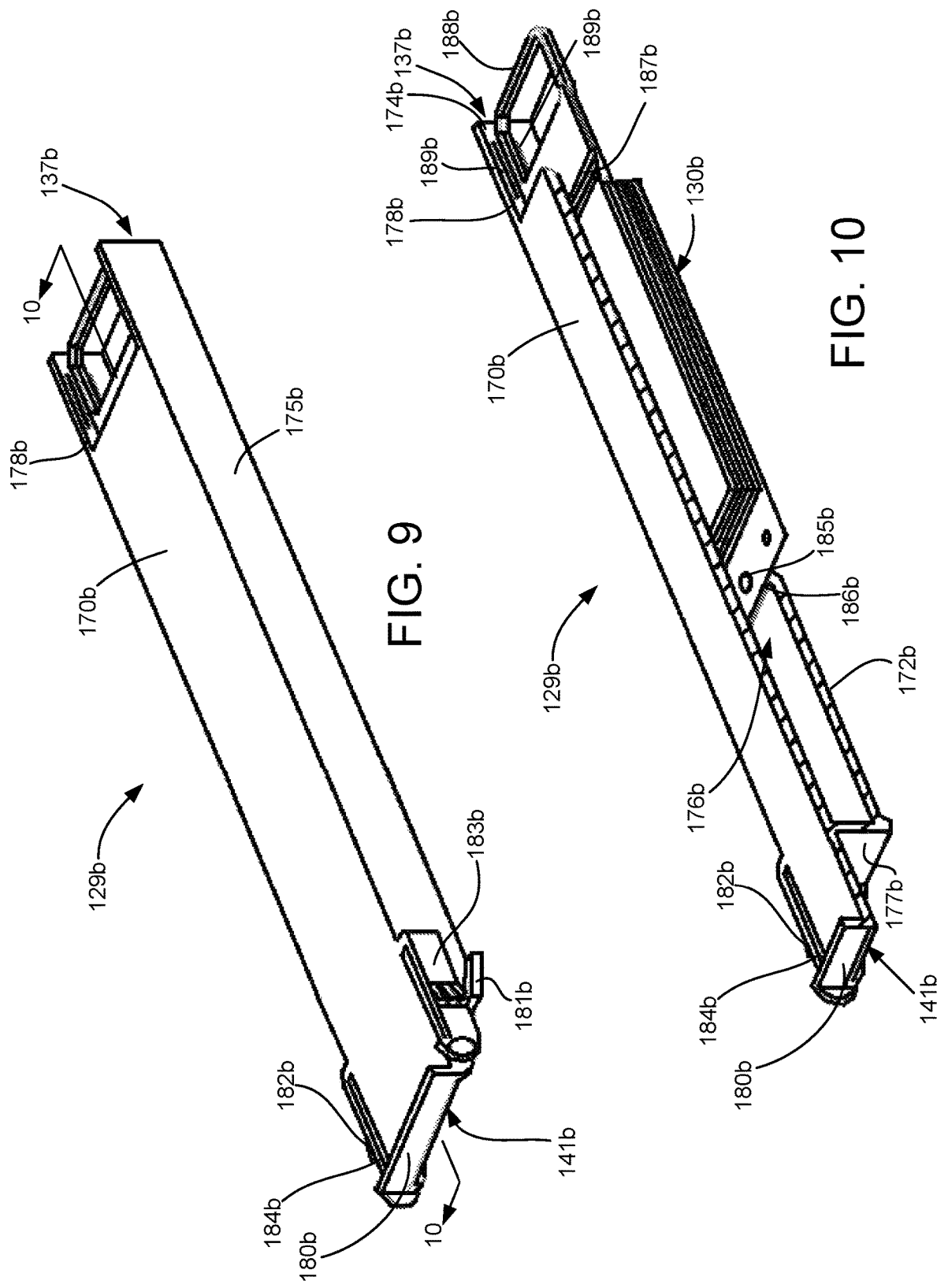

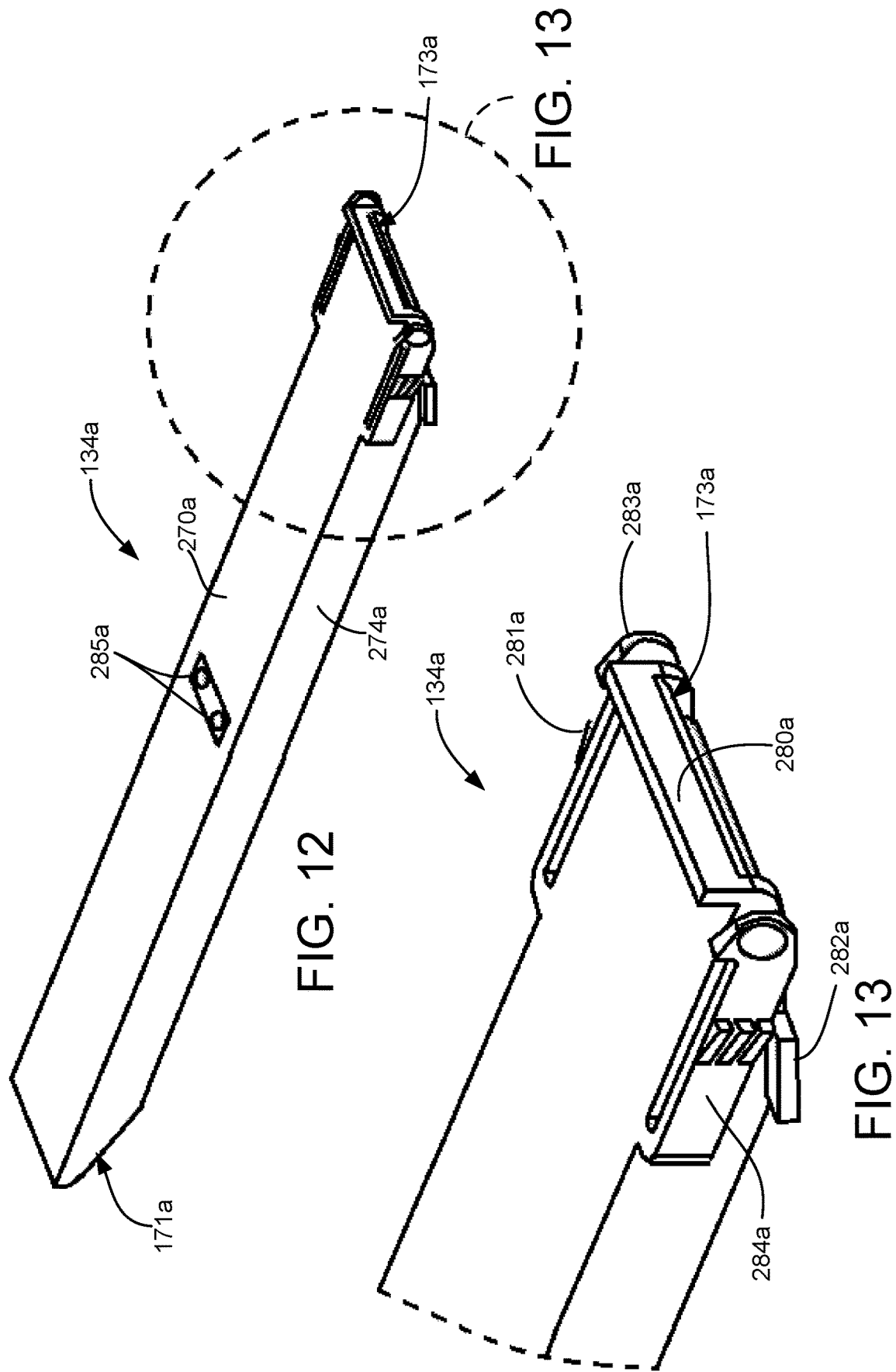

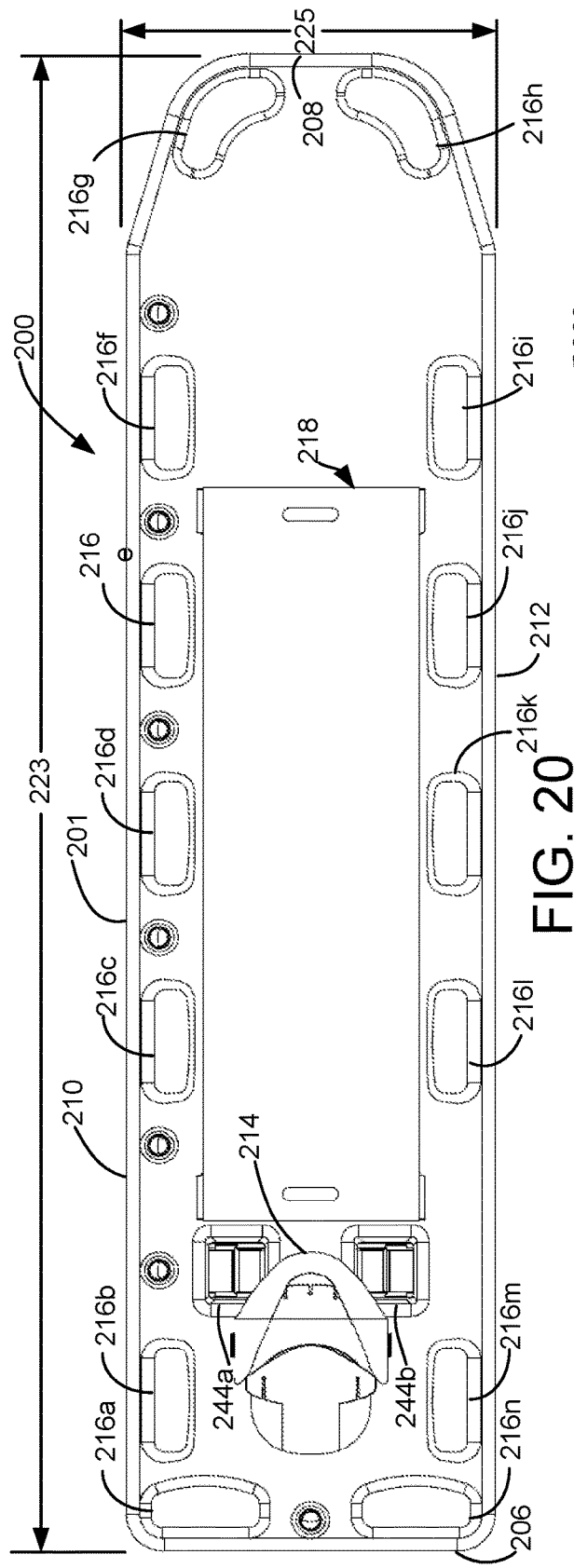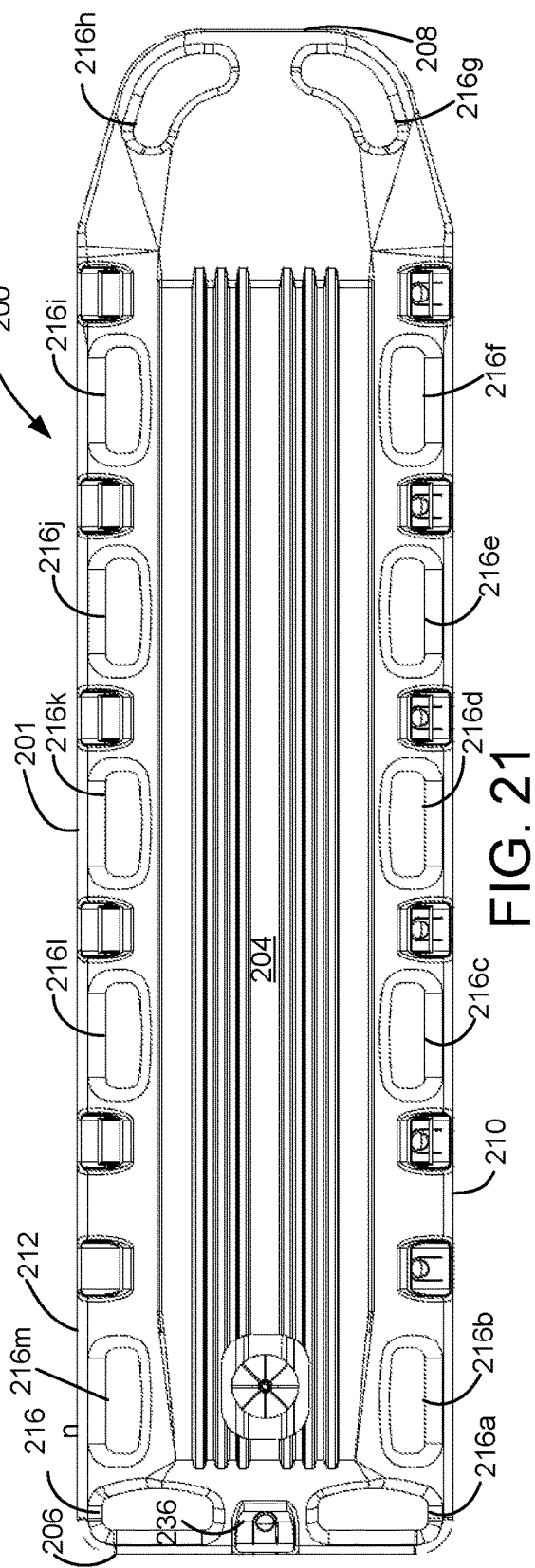

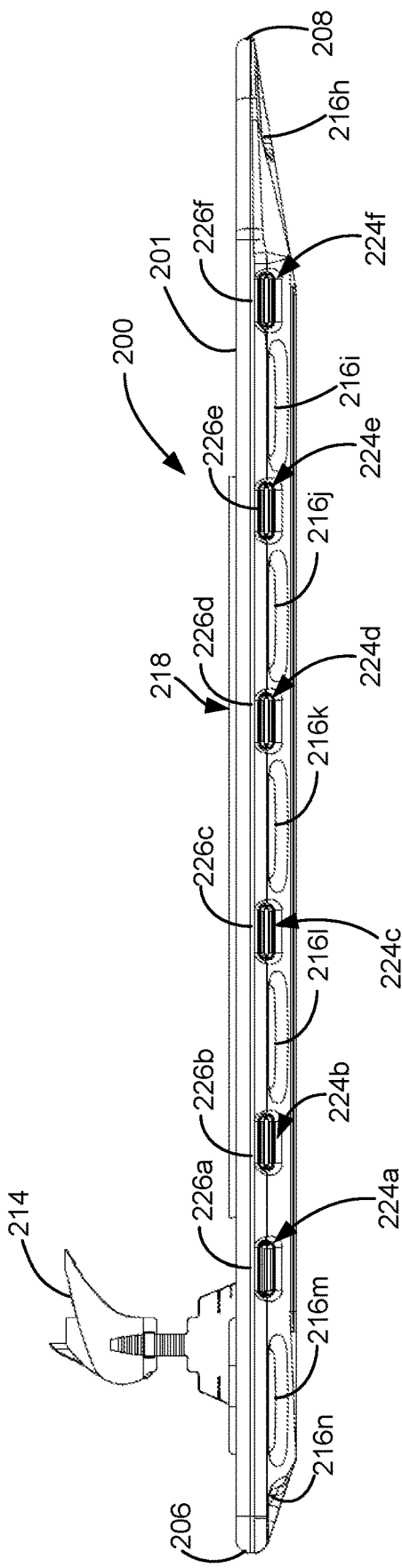
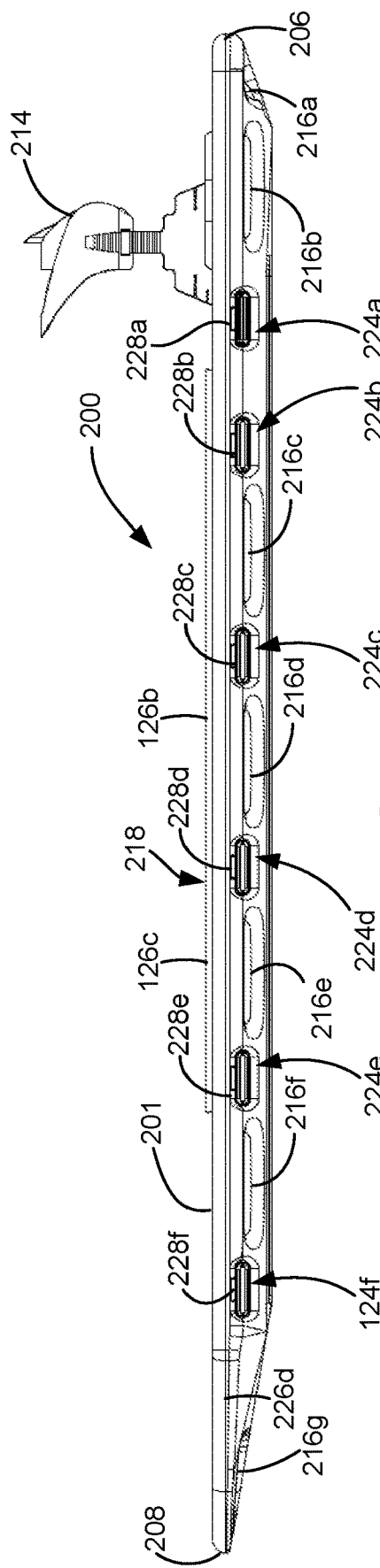
FIG. 22
FIG. 23

REMOVABLE CARTRIDGES FOR A SPINE BOARD

CROSS REFERENCE TO RELATED APPLICATION

The present application is a continuation of and claims priority to U.S. patent application Ser. No. 15/707,435, filed on Sep. 18, 2017, which is based on and claims the benefit of U.S. patent application Ser. No. 14/792,981, filed Jul. 7, 2015, now U.S. Pat. No. 9,763,838 issued Sep. 19, 2017, which is based on and claims the benefit of U.S. provisional patent application Ser. No. 62/022,308, filed Jul. 9, 2014, the content of which is hereby incorporated by reference in their entireties.

BACKGROUND

Spine boards are patient handling devices that provide rigid support to prevent further injury of a patient while the patient is being transported to a medical center for treatment. They are commonly used by medical personnel during emergency and rescue situations so as to provide increased efficiency and effectiveness in performing the vital tasks required.

The discussion above is merely provided for general background information and is not intended to be used as an aid in determining the scope of the claimed subject matter.

SUMMARY

A removable cartridge is configured to be inserted into a receiving channel. The cartridge includes an elongated body having a leading end, a trailing end, a top surface and a bottom surface. The leading end is inserted into the receiving channel before the trailing end. A button protrudes from the top surface of the elongated body and is positioned proximate the trailing end of the elongated body. When the cartridge is being inserted into the receiving channel, the button is compressed. After the cartridge is inserted into the receiving channel, the button releases into an opening that intersects with the receiving channel so as to lock the cartridge in the channel.

A removable cartridge is configured to be inserted into a receiving channel. The cartridge includes an elongated hollow body having an outer surface including a leading end, a trailing end, a top surface and a bottom surface. The leading end is inserted into the receiving channel before the trailing end. The cartridge also includes at least two openings that extend from the outer surface of the elongated hollow body to a hollow interior of the elongated hollow body. The hollow interior of the elongated hollow body holds at least one safety strap having a first end and a second end. A first end of the at least one strap exits through one of the two openings and a second end of the at least one strap exits through the other of the two openings.

A removable cartridge is configured to be inserted into a receiving channel. The cartridge includes an elongated body having a leading end, a trailing end, a top surface, a bottom surface, a first side and an opposing second side. The leading end is inserted into the receiving channel before the trailing end. The elongated body includes a pair of prongs that extend from the leading end to a terminating point along the elongated body. The first prong of the pair of prongs extends along the first side of the elongated cartridge and has an interior facing surface. The second prong of the pair of prongs extends along the opposing second side of the elongated cartridge, has an interior facing surface that faces the interior facing surface of the first prong and is spaced apart from the first prong by a distance. The interior facing surfaces of the pair of prongs are configured to hold another component that intersects with the receiving channel in place.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 4 is a right side view of FIG. 1.

FIG. 5 is a left side view of FIG. 1.

FIG. 9 is a perspective view of an exemplary longitudinal cartridge that is to be located in an exemplary longitudinal channel in the spine board according to one embodiment.

FIG. 10 is a perspective section view of the exemplary longitudinal cartridge in FIG. 9 taken through the line indicated in FIG. 9 and illustrating a strap housed by the exemplary longitudinal cartridge according to one embodiment.

FIG. 12 is a perspective view of an exemplary lateral cartridge that is to be located in an exemplary lateral channel in the spine board according to one embodiment.

FIG. 13 is an enlarged view of the trailing end of the exemplary lateral cartridge illustrated in FIG. 12.

FIG. 20 is a top view of FIGS. 18 and 19.

FIG. 21 is a bottom view of FIGS. 18 and 19.

FIG. 22 is a right side view of FIGS. 18 and 19.

FIG. 23 is a left side view of FIGS. 18 and 19.

DETAILED DESCRIPTION

The following embodiments describe a support article or spine board that provides increased efficiency and effectiveness in performing the vital tasks required by medical personnel in treating patients who have sustained physical injury. The support article or spine board includes an adjustable brace or cervical collar that can be fitted around the patient's neck before being positioned and locked into the board and preloaded straps in cartridges located in channels within the main body of the board. Together these components provide medical personnel with the ability to secure and constrain patients during transport so as to prevent further injury as well as provide medical personnel with the ability to apply preventative treatments immediately so as to limit the severity of injury.

Figure 1:
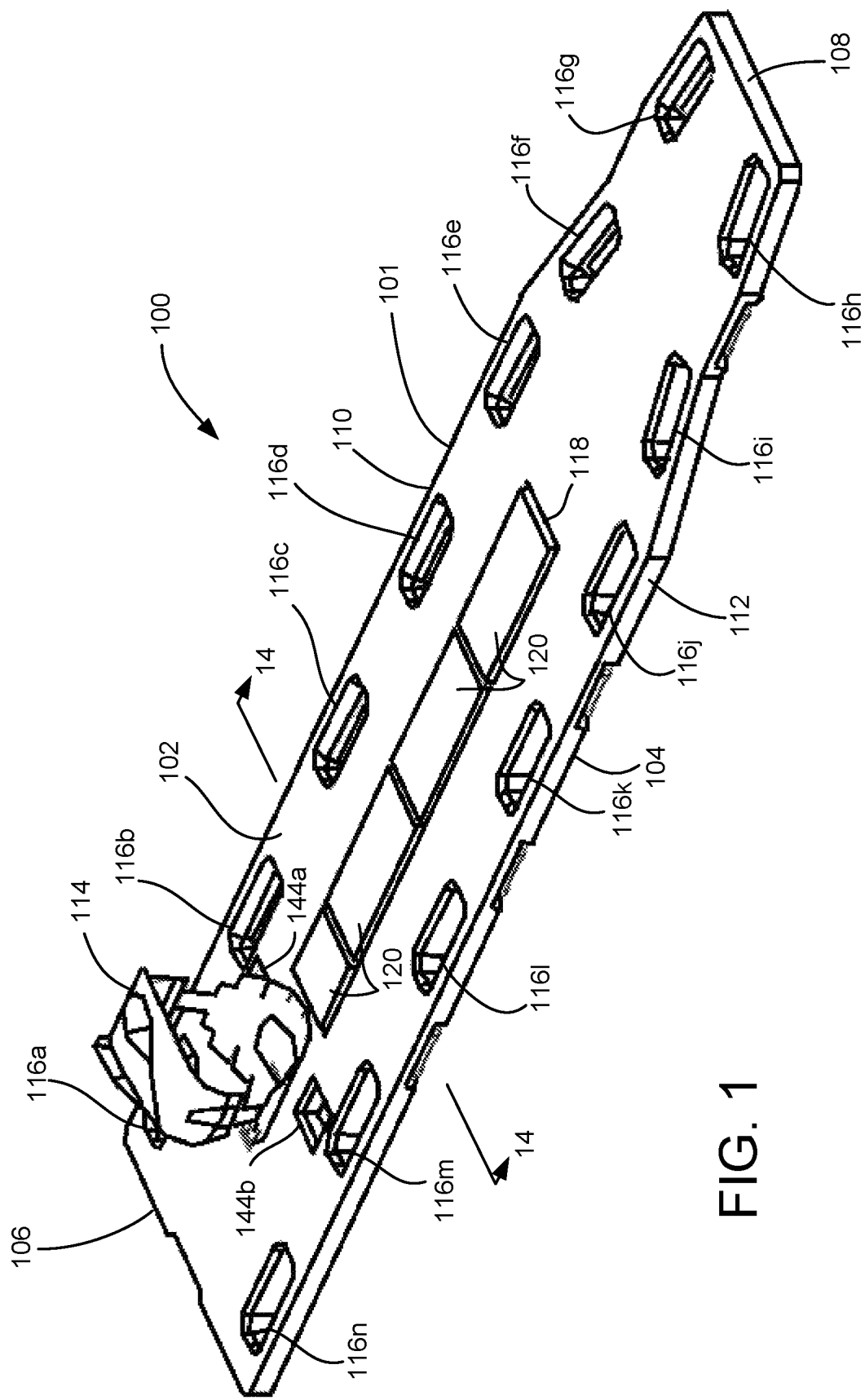
FIG. 1 is a perspective view illustrating a spine board and a cervical collar mounted to the spine board according to one embodiment.

FIG. 1 is a perspective view of a support article or spine board 100. FIGS. 2-7 are a top view, a bottom view, a right side view, a left side view, a back view and a front view of spine board 100. Board 100 includes and contains multiple features that are required to treat patients at the scene of an emergency by first responders and allows for the most efficient use of those features to drastically reduce the amount of critical time needed to prepare the injured person for transport to a medical facility. Board 100 and its multiple features is easily cleaned, has intuitive use, limited parts and is equipped with replaceable components.

Spine board 100 includes a main body 101 having a top surface 102, an opposing bottom surface 104, a first end 106, an opposing second end 108, a first longitudinal side 110 and an opposing second longitudinal side 112. The distance between top surface 102 and bottom surface 104 defines a thickness 127 (FIG. 6) of main body 101. The distance between first end 106 and second end 108 defines a length 123 (FIG. 2) of main body 101. The distance between first longitudinal side 110 and second longitudinal side 112 defines a width 125 (FIG. 6) of main body 101. First and second longitudinal sides 110 and 112 connect first and second ends 106 and 108. In one embodiment, spine board 100 is made of a light-weight synthetic material, durable enough to withstand years of use by medical personnel.

Spine board 100 includes an adjustable brace or cervical collar 114 mounted to main body 101 that protrudes from top surface 102, a plurality of grasping handles 116a-n and an ice tray 118. Cervical collar 114 is fitted around a patient's neck and then fixed to board 100 prior to patient transport to prevent as much movement of the spine as possible. A collar stabilization key 136 (FIGS. 2-3 and 6) is located internal to main body 101 of board 100 and is used to hold the cervical collar 114 in place and prevent motion of the head and neck in multiple directions. Cervical collar 114 and collar stabilization key 136 will be discussed in more detail below.

Handles 116a-n are spaced apart from each other and are placed in locations adjacent to and along first longitudinal side 110 and second longitudinal side 112 to allow medical personnel to carry spine board 100. Along the mid-section of main body 101 of board 100 is ice tray 118 that is recessed from top surface 102 of main body 101 and, in one embodiment, is configured to receive ready-to-use chemically activated cold packs 120, which can be activated if the patient requires such treatment along the back. These can be utilized at the discretion of the emergency responder if the patient requires such treatment for their injuries. Recessed ice tray 118 holds the cold packs 120 in place. In one embodiment, the top surfaces of cold packs 120 may protrude from top surface 102 of main body 101 and, in another embodiment, can be held in place with hook and loop material.

Also incorporated into the board are a plurality of channels and a plurality of cartridges that are inserted in the channels and contain straps. The channels exist within main body 101 and are located interior to the outer surfaces of board 100 including between top surface 102 and bottom surface 104 and between first end 106 and second end 108 and between first longitudinal side 110 and second longitudinal side 112. The channels provide openings to receive the cartridges, which contain the straps that secure the patient to the board. The cartridges are single use units that are loaded and stored within the board and provide easy access to the straps when needed for treatment of the patient.

Figure 2:
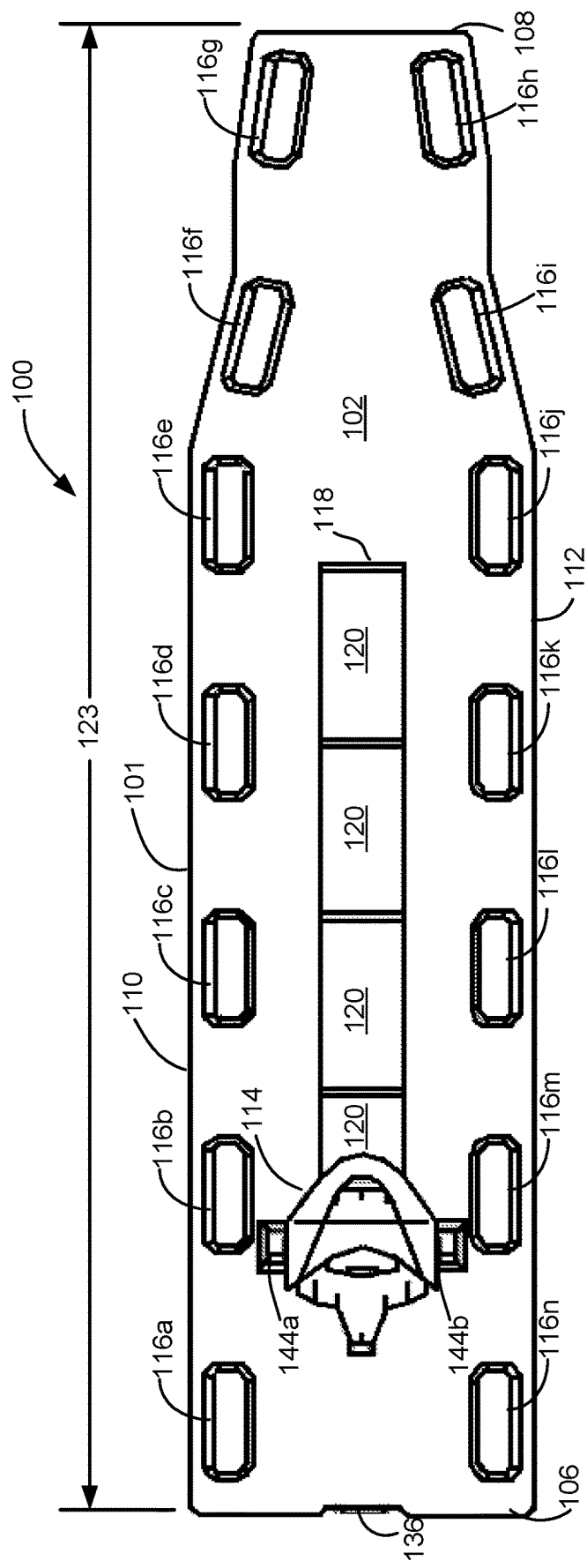
FIG. 2 is a top view of FIG. 1.
Figure 3:
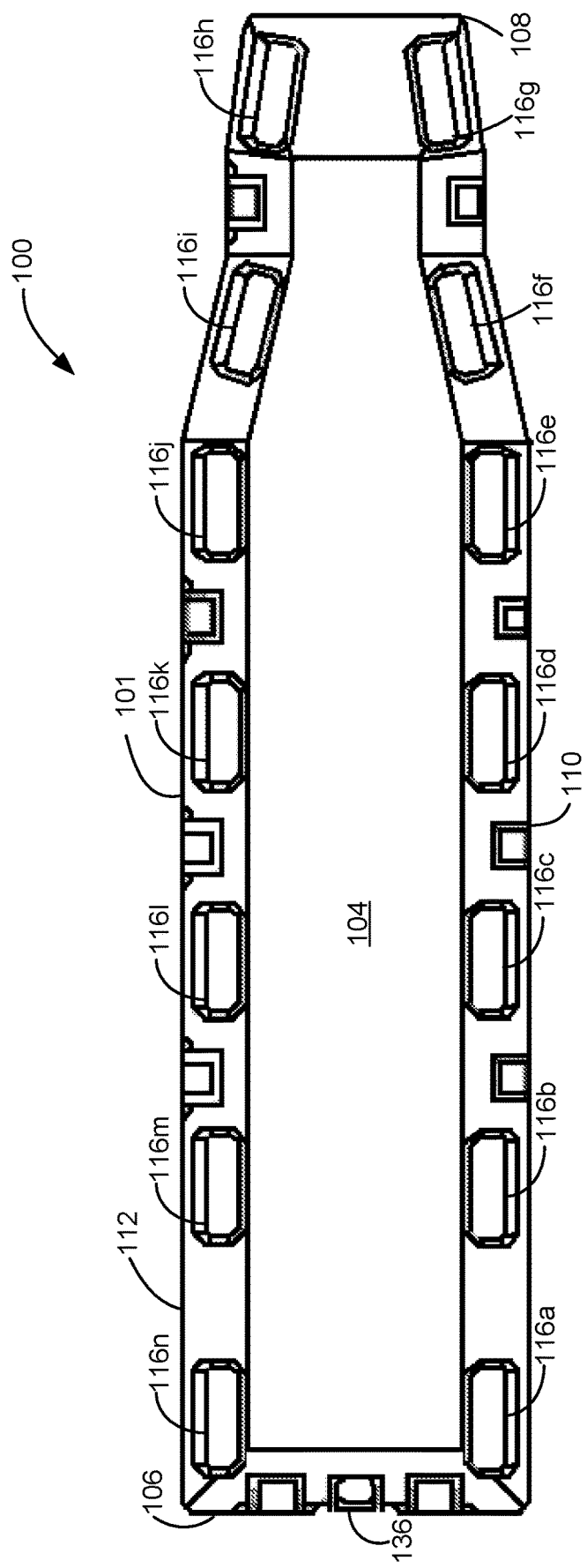
FIG. 3 is a bottom view of FIG. 1.
Figure 6:
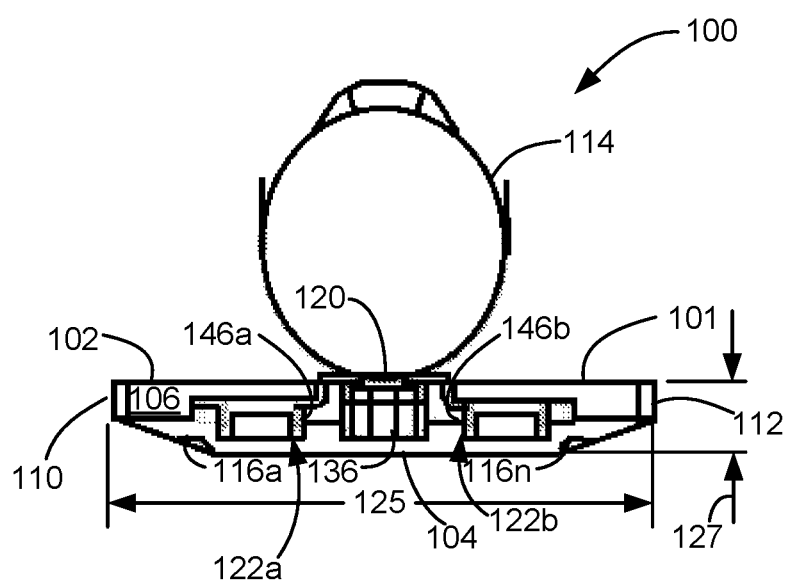
FIG. 6 is a back view of FIG. 1.
Figure 7:
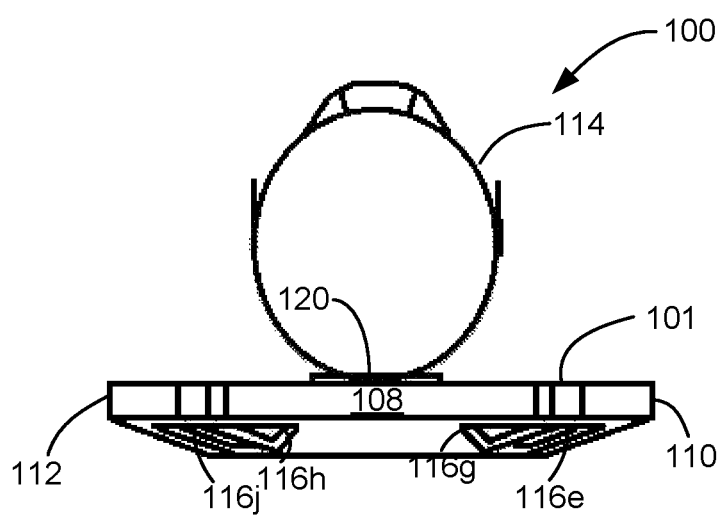
FIG. 7 is a front view of FIG. 1.

In one embodiment, there are two different types of channels that exist within main body 101 of board 100. First, a pair of longitudinal channels 122a-b (FIG. 6 and better shown in FIG. 8) that extend longitudinally along a portion of length 123 of spine board 100 (i.e., along either side of cervical collar 114) from first end 106 to second ends 144a and 144b (FIGS. 1 and 2). Second, a plurality of lateral channels 124a-d (FIGS. 4 and 5) that extend laterally through width 125 of main body 101 from first longitudinal side 110 to second longitudinal side 112.

Figure 8:
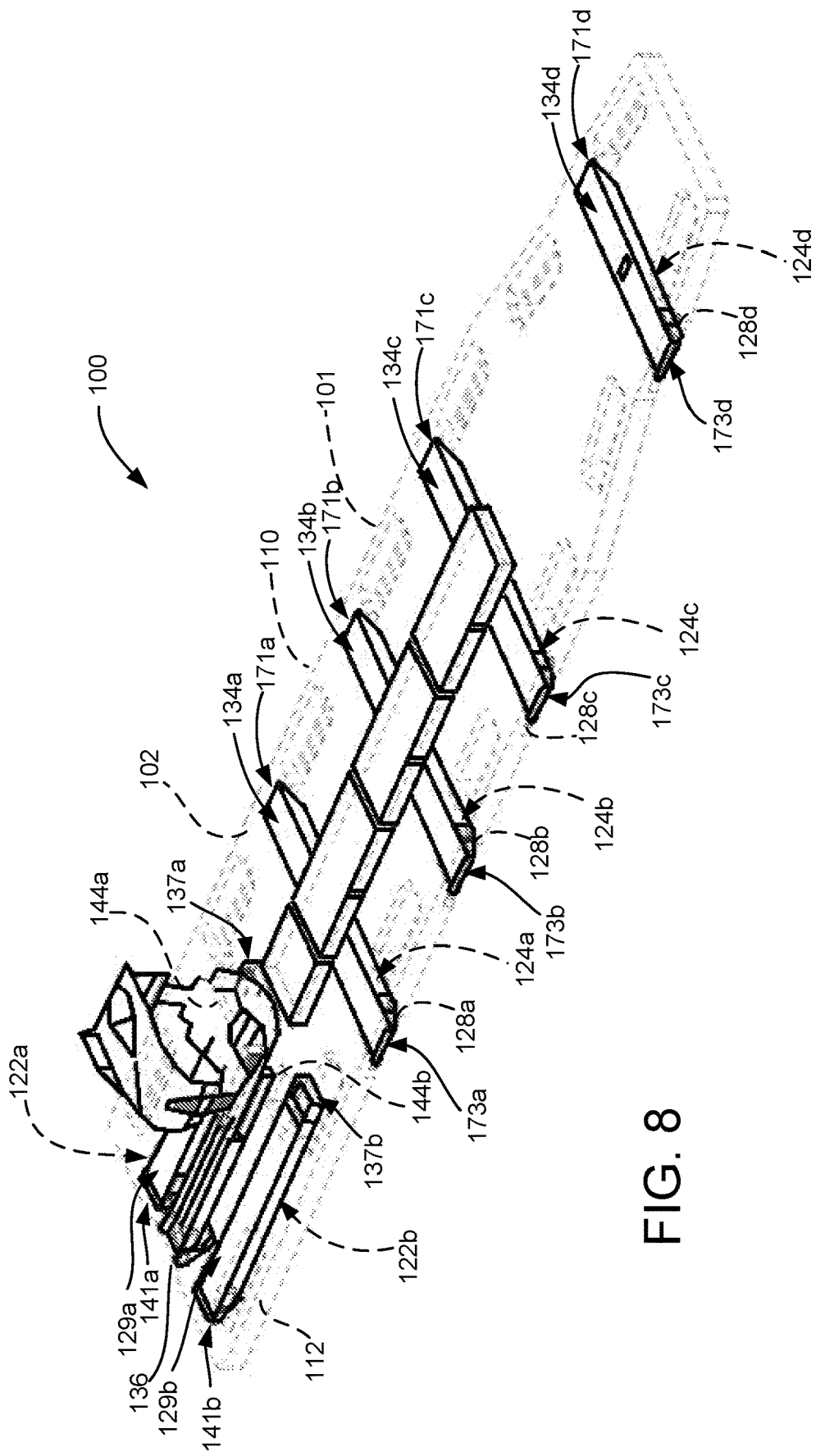
FIG. 8 is the perspective view illustrated in FIG. 1 with the spine board shown in phantom to illustrate internal components.

FIG. 8 is the perspective view of spine board 100 in FIG. 1 with main body 101 shown in phantom to illustrate internal components. Longitudinal channels 122a and 122b are located inside main body 101 between top surface 102 and bottom surface 104 and have open second ends or exit ends 144a and 144b, respectively, and open first ends or insertion ends 146a and 146b (FIG. 6), respectively. Open first ends 146a and 146b intersect with first end 106 of main body 101 and serve as the insertion openings into channels 122a-b for cartridges 129a and 129b. Open second ends 144a and 144b intersect with top surface 102 of main body 100 and serve as exit ends for straps stored in cartridges 129a and 129b. First longitudinal channel 122a and second longitudinal channel 122b are spaced apart from first and second longitudinal sides 110 and 112 of main body 101 and from each other. First longitudinal channel 122a is located in closer proximity to first longitudinal side 110 than second longitudinal side 112. Second longitudinal channel 122b is located in closer proximity to second longitudinal side 112 than first longitudinal side 110. Longitudinal channels 122a and 122b extend for a length from first end 106 of main body 101 to open second ends 144a and 144b, which are in an area proximal to where cervical collar 114 is attached to main body 101.

Lateral channels 124a, 124b, 124c and 124d are oriented substantially perpendicular to longitudinal channels 122a-b, but do not intersect longitudinal channels 122a-b since they are spaced away from longitudinal channels 122a-b. Lateral channels 124a-d are also located inside main body 101 between and spaced apart from top surface 102 and bottom surface 104, have a length that is a width of main body 101, are spaced apart from each other along length 123 of main body 101 and have open first ends 126a, 126b, 126c and 126d that intersect with first longitudinal side 110 and open second ends 128a, 128b, 128c and 128d that intersect with second longitudinal side 112. Both open first ends 126a-d and open second ends 128a-d serve as exit ends for straps stored in cartridges 134a-d.

As illustrated and as previously discussed, longitudinal channels 122a-b and lateral channels 124a-d that exist within main body 101 of spine board 100 house and store removable cartridges that contain straps. Longitudinal channels 122a-b receive and house first and second longitudinal cartridges 129a and 129b having leading ends 137a and 137b and trailing ends 141a and 141b, respectively. Lateral channels 124a-d receive and house lateral cartridges 134a, 134b, 134c and 134d having leading ends 171a-d and trailing ends 173a-d, respectively. Each cartridge 129a-b and 134a-d contain and store a strap used to secure the patient to main body 101 of board 100. The straps are made with hook and loop material for securing via attachment onto themselves.

FIG. 9 is a perspective view of exemplary longitudinal cartridge 129b that is to be removably inserted in exemplary longitudinal channel 122b according to one embodiment. FIG. 10 is a perspective section view of exemplary longitudinal cartridge 129b taken through the line indicated in FIG. 9 to show strap 130b housed and stored in exemplary cartridge 129b according to one embodiment. Exemplary longitudinal cartridge 129b is substantially identical to longitudinal cartridge 129a, which is located in longitudinal channel 122a, so features described with respect to cartridge 129b should be applied to cartridge 129a.

As previously discussed, longitudinal cartridge 129b includes a leading end 137b and a trailing end 141b. When placed in longitudinal channel 122b, leading end 137b is located at open second end 144b and trailing end 141b is located at open second end 146b. Trailing end 141b includes flanges 180b, 181b and 182b (substantially identical to flange 181b) and a pair of substantially identical spring or barbed clips 183b and 184b. Flanges 180b, 181b and 182b and spring clips 183b and 184b engage with recesses in main body 101 for locking longitudinal cartridge 129b into channel 122b of main body 101. Longitudinal cartridge 129b further includes a top wall 170b, a bottom wall 172b, a first side wall 174b and a second side wall 175b. Together, top wall 170b, bottom wall 172b, first side wall 174b and second side wall 175b define a compartment 176b for containing and storing strap 130b. Compartment 176b is also defined between a trailing end wall 177b located proximal to trailing end 141b of longitudinal cartridge 129b and an opening 178b in leading end 137b of longitudinal cartridge 129b. Opening 178b provides access to strap 130b and aligns with second end 144b of channel 122b in main body 101 of board 100.

As illustrated in FIG. 10, strap 130b is stored in cartridge 129b in a single serpentine arrangement of hook and loop strap material (i.e., strap 130b is folded over and onto itself) and is secured to bottom wall 172b of compartment 176b at a first end 186b of strap 130b with at least one fastener 185b, such as one more rivets. Second end 187b of strap 130 includes a finger hook 188b. Finger hook 188b is secured to the interior facing walls 174b and 175b of compartment 176b with ribs 189b so as to prevent accidental or premature removal of strap 130b from cartridge 129b. However, other ways of securing finger hook 188b to interior facing walls 174b and 175b are possible.

Figure 11:
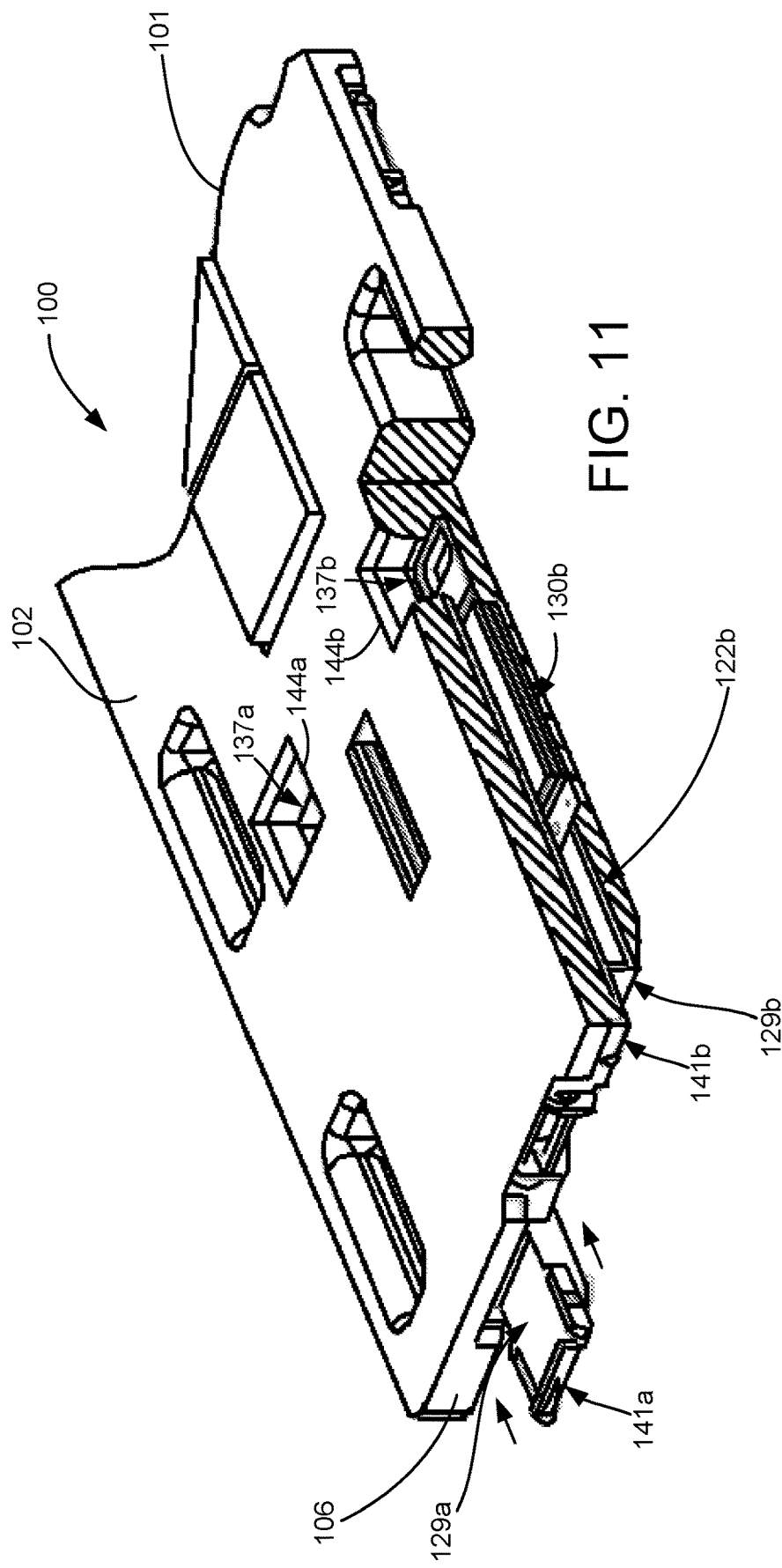
FIG. 11 is a partial perspective view of a section of the spine board illustrating the insertion of and placement of longitudinal cartridges in the main body of the spine board.

FIG. 11 is a partial perspective view of a section of spine board 100 illustrating the removable insertion of and placement of longitudinal cartridges 129a and 129b in main body 101 of spine board 100. As illustrated by longitudinal cartridge 129a, the leading ends 137a and 137b of the longitudinal cartridges 129a and 129b are inserted into channels 122a and 122b, respectively, at first end 106 of main body 101 and are slid along the lengths of channels 122a and 122b in the direction illustrated by the exemplary directional arrows until leading ends 137a and 137b reach second ends 144a and 144b of channels 122a and 122b. Second ends 144a and 144b of channels 122a and 122b are strap access cavities 144a and 144b, which are open to and communicate with top surface 102 of main body 101. As longitudinal cartridges 129a and 129b reach their full insertion position, the spring or barbed clips on trailing ends 141a-b will become compressed and as insertion is completed the spring or barbed clips will click into position, thereby indexing with main body 101 and holding cartridges 129a-b in place. The spring or barbed clips prevent the longitudinal cartridges 129a and 129b from being removed accidentally and additionally keep the longitudinal cartridges 129a and 129b in position as straps are removed for use on the patient.

The straps contained and stored in longitudinal cartridges 129a and 129b, such as a first longitudinal strap stored in first longitudinal cartridge 129a and a second longitudinal strap stored in second longitudinal cartridge 129b, are pulled from leading ends 137a and 137b and through strap access cavities 144a and 144b using the fingers hooks on the second ends of the straps, such as finger hook 188b of strap 130b. After the first longitudinal strap in longitudinal cartridge 129a is pulled out of cartridge 129a it is brought over a left shoulder of a patient and secured as described in detail below. After second longitudinal strap 130b in longitudinal cartridge 129b is pulled out of cartridge 129b it is brought over a right shoulder of the patient and secured as described in detail below. Therefore, the longitudinal straps stored in longitudinal cartridges 129a and 129b are used to secure the chest area of a patient by forming a cross shape across their chest after each strap is pulled out of each longitudinal cartridge 129a-b at exit ends 144a and 144b or strap access cavities 144a and 144b. In the alternative, the longitudinal straps do not necessarily have to cross the chest of the patient and can separately secure the right and left side of a patient's torso to the spine board. As illustrated and previously discussed, exit ends or strap access cavities 144a and 144b of longitudinal channels 122a and 122b are located in an area proximal cervical collar 114. The securing of the patient using the longitudinal straps will be discussed in more detail below.

FIG. 12 is a perspective view of exemplary lateral cartridge 134a that is to be removably inserted in exemplary lateral channel 124a according to one embodiment. FIG. 13 illustrates an enlarged view of trailing end 173a of lateral cartridge 134a in FIG. 12. Exemplary lateral cartridge 134a is substantially identical to lateral cartridges 134b and 134c (FIG. 2) and is similar to lateral cartridge 134d (FIG. 2) in that the structure is substantially identical, but lateral cartridge 134d is shorter than lateral cartridges 134a-c because lateral channel 124d is shorter than lateral channels 124a, 124b and 124c. Still further, each hook and loop strap located in each lateral cartridge 134a-c are substantially identical, however, the hook and loop strap located in lateral cartridge 134d is shorter than the straps in lateral cartridges 134a-c. Therefore, features described with respect to cartridge 134a should also be applied to cartridges 134b-d.

As previously discussed, each lateral cartridge 134a-d includes leading end 171a-d and trailing end 173a-d. When placed in lateral channels 124a-d, leading end 171a-d are located at open first ends 126a-d and trailing ends 173a-d are located open second ends 128a-d. Each trailing end 173a-d includes flanges and a pair of substantially identical spring clips that engage with recesses in main body 101. As illustrated by the exemplary lateral cartridge 134a in FIGS. 12 and 13, trailing end 173a of lateral cartridge 134a includes flanges 280a, 281a and 282a (which is substantially identical to flange 281a) and pair of substantially identical spring clips 283a and 284a. Flanges 280a, 281a and 282a and spring clips 283a and 284a engage with recesses in main body 101 for locking lateral cartridge 134a into channel 124a of main body 101.

Figure 14:
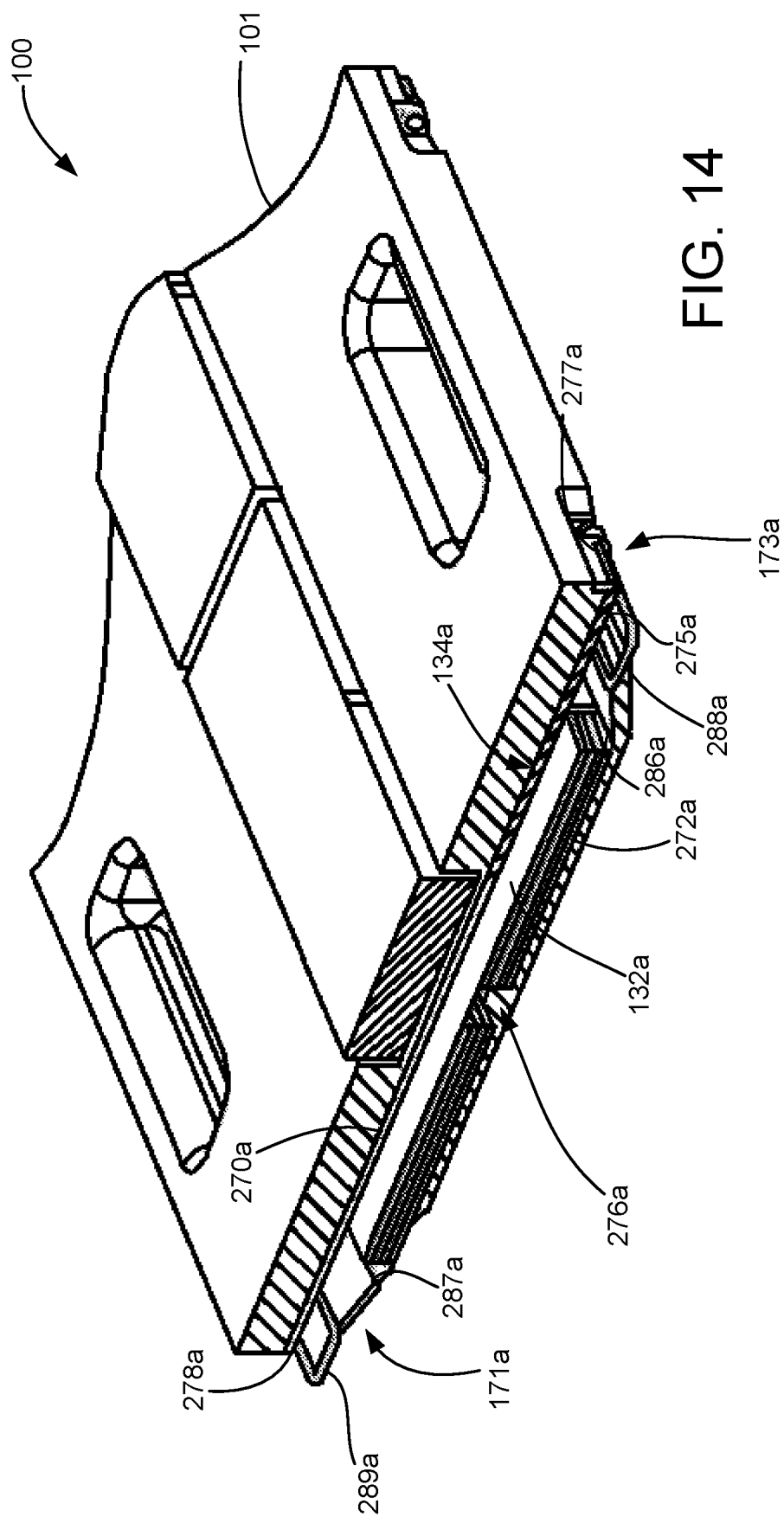
FIG. 14 is a partial perspective view of a section of the spine board illustrating the placement of the exemplary lateral cartridge in the main body of the spine board.

FIG. 14 is a partial perspective view of a section of main body 101 of spine board 100 taken through the line indicated in FIG. 1 and illustrating the exemplary placement of exemplary lateral cartridge 134a in main body 101 of spine board 100. Each lateral cartridge 134a-d further includes a compartment for containing and storing a lateral strap made of hook and loop material. As illustrated in FIGS. 12 and 14, lateral cartridge 134a includes a compartment 276a defined by a top wall 270a, a bottom wall 272a, a first side wall 274a, a second side wall 275a, a trailing end opening 277a located proximal to trailing end 173a and a leading end opening 278a located proximal to leading end 171a. Openings 277a and 278a provide access to lateral strap 132a.

In particular, each lateral strap is stored in each lateral cartridge 134a-d in a dual serpentine arrangement of hook and loop strap material (i.e., a dual arrangement of strap material folded over and onto itself) with the center of each lateral strap secured to the center of the top wall of each lateral cartridge 134a-d so as to prevent the entirety of each lateral strap from exiting from each lateral cartridge 134a-d. In this way, a first end of each lateral strap can exit out a leading end of each lateral cartridge and each second end of each lateral strap can exit out a trailing end of each lateral cartridge. For example, in FIGS. 12 and 14, lateral strap 132a includes first end 286a and second end 287a with equal lengths of strap formed into first and second serpentine arrangements and the center of lateral strap 132a secured to top wall 270a using at least one fastener 285a, such as one more rivets. In addition, each lateral strap located in each lateral cartridge 134a-d includes finger hooks located at their ends. First end 286a of strap 132a includes a first end finger hook 288a and second end 287a of strap 132a includes a second end finger hook 289a. First end finger hook 288a is secured to trailing end 173a of lateral cartridge 134a and second end finger hook 289a is secured to leading end 171a of lateral cartridge 134a when lateral strap 132a is not in use so as to prevent accidental or premature removal of both sides of the strap 132a from cartridge 134a.

As illustrated in FIG. 8, to insert and place lateral cartridges 134a-d in main body 101 of spine board 100, the leading ends 171a-d of lateral cartridges 134a-d are inserted into channels 124a-d, respectively, and are slid from second longitudinal side 112 of main body 101 to first longitudinal side 110 until leading ends 171a-d reach first longitudinal side 110. As lateral cartridges 134a-d reach their full insertion position, the spring or barbed clips on trailing ends 173a-d will become compressed and as insertion is completed the spring or barbed clips will click into position, thereby indexing with main body 101 and holding cartridges 134a-d in place. The spring or barbed clips prevent the lateral cartridges 134a-d from being removed accidentally and additionally keep the lateral cartridges 134a-d in position as straps are removed for use on the patient. Still further, the flanges, such as flanges 280a, 281a and 282a (FIG. 13) provide a hard stop, which prevents cartridges 134a-d from passing completely through main body 101 of board 100.

Each strap contained and stored in each lateral cartridge 134a-d, such as strap 132a, includes a first end that is pulled from the leading end 171a-d and a second end that is pulled from the trailing end 173a-d using the finger hooks on the first and second ends of the straps, such as finger hook 289a located on second end 287a of strap 132a and finger hook 288a located on first end 286a of strap 132a. The straps, made of hook and loop material, are wrapped around the patient and placed on top of themselves or each other to secure the patient's torso, waist and legs to the board. Although unnecessary, it is possible to further thread the straps through the handles by twisting the strap at the handle to allow for hook and loop surfaces to contact each other. All four straps in all four lateral cartridges 134a-d should be utilized to securely fasten the patient to spine board 100. In regards to securing the longitudinal straps in longitudinal cartridges 129a and 129b, the longitudinal straps are brought over the shoulders of the patient, crossed and are attached via its hook and loop material to the lateral straps that were wrapped around the patient. In one embodiment, the load to the longitudinal straps will be divided across multiple lateral straps. If additional strength is required, then the longitudinal straps can be threaded through any of handles 116 to provide further strength.

For sanitation purposes, both longitudinal cartridges 129a-b and lateral cartridges 134a-d including the straps that they house are single use and are removed for replacement. Cartridges 129a-b and 134a-d are easily removed from main body 101 by grasping the spring or barbed clips, such as 183b and 184b and 283a and 284a, and squeezing them toward the center of the respective cartridge while pulling the respective cartridge from main body 101.

Figure 15:
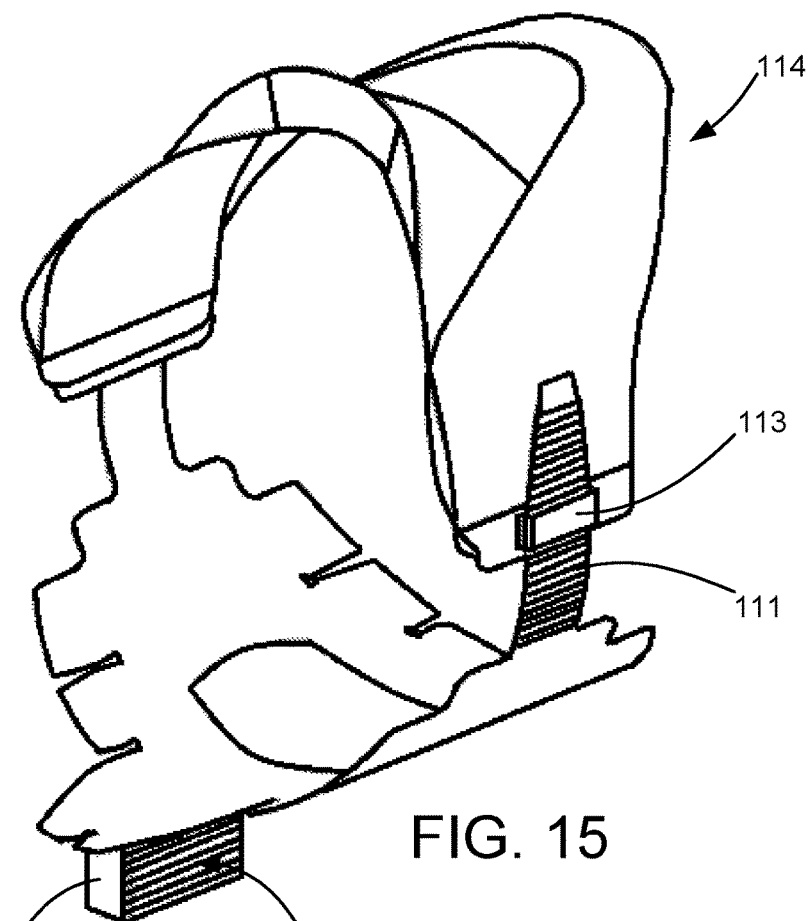
FIG. 15 is a perspective view of a cervical collar according to one embodiment.

FIG. 15 is a perspective view of cervical collar 114. Cervical collar 114 is composed of different density polyethylene plastic materials based on function. Use of polymer-type materials will be apparent to one of skill in the art. A high density polyethylene provides structural strength when surrounding the cervical portion of the spine as well as provides strength for post 115, which is attached to the back of collar 114. A polyethylene foam provides a pad to the contact areas. An ice pack can also pad the contact areas and will provide a therapeutic cooling effect to the cervical area confined to collar 114 (if activated). Collar 114 stores in a low, flat profile and assumes a three-dimensional configuration when wrapped around the patients neck and secured with a pair of saw tooth straps and corresponding buckles. In addition, collar 114 and post 115 are radiolucent to allow x-rays to be taken without removal of the patient from the collar or the spine board. In another embodiment, collar 114 can contain phosphors for radiating visible light after being energized so as to be "glow-in-the-dark." Collar 114 is designed to be slid under the arch of the subject's neck. It is secured to the patient using a saw tooth strap 111 and buckle 113 configuration and secured to main body 101 of board 100 using post 115 that has exterior facing grooves or indexing slots 109. It should be realized that other ways to secure collar to a patient's neck are possible. In another embodiment, cervical collar 114 has multiple distal contact points including, but not limited to contact points with the bilateral clavicles, bilateral trapezius muscles, the sternum, posterior soft tissues overlying the occiput and anteriorly the mandible and its soft tissue.

Figure 16:
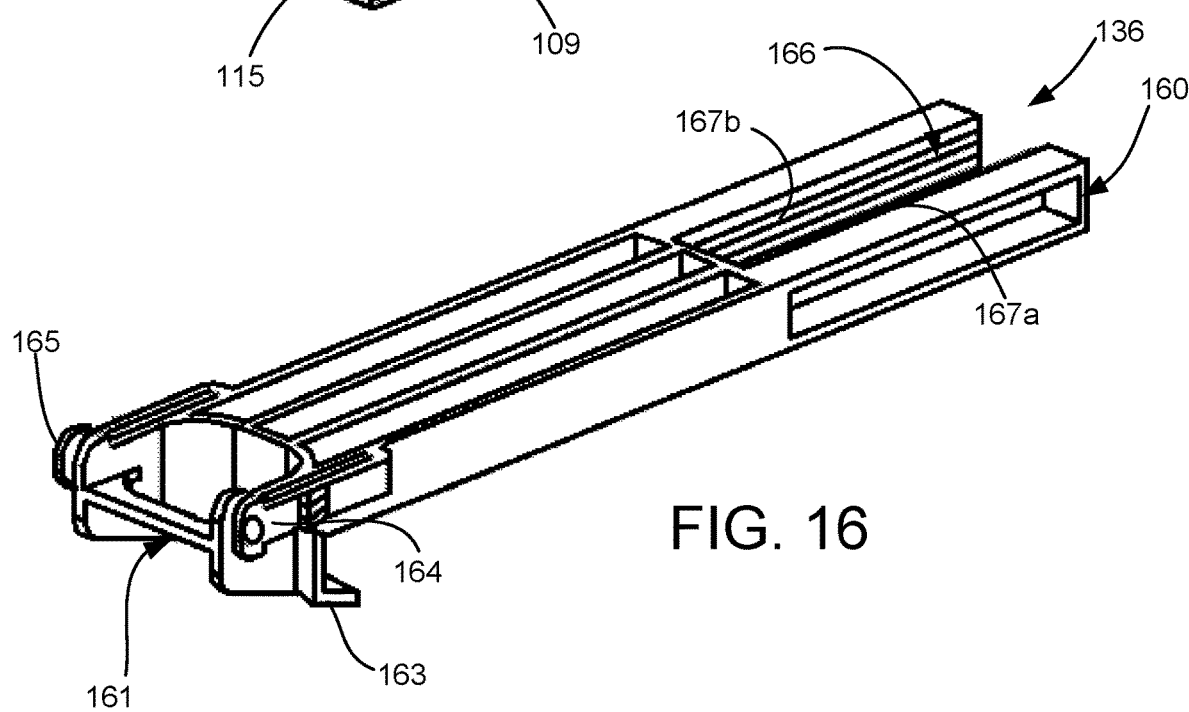
FIG. 16 is a perspective view of a collar stabilization key for securing the cervical collar of FIG. 15 to the spine board according to one embodiment.

As previously discussed, cervical collar 114 contains at least two features: a chemically activated cold pack embedded within the collar that can be activated by medical personnel if the situation calls for it, and supporting post 115 that can be inserted into an opening 117 in main body 101 of board 100 and locked into place with collar stabilization key 136. FIG. 16 is a perspective view of collar stabilization key 136. Collar stabilization key 136 includes a leading end 160 and a trailing end 161. Trailing end 161 includes a flange 163 that is for engaging with main body 101 of board 100. Trailing end 161 also includes a pair of spring or barbed clips 164 and 165. Extending from leading end 161 and less than halfway to trailing end 161 is a passage 166 having interior facing sides with grooves or indexing slots 167a and 167b that face each other. Indexing slots 167a and 167b are for engaging with the grooves or indexing slots 109 on either side of the exterior facing surfaces of post 115. Providing post 115 with varying heights of indexing slots 109 and collar stabilization key 136 with varying heights of indexing slots 167a and 167b allow for the patient's head to be positioned above top surface 102 of board 100 should it be required.

Figure 17:
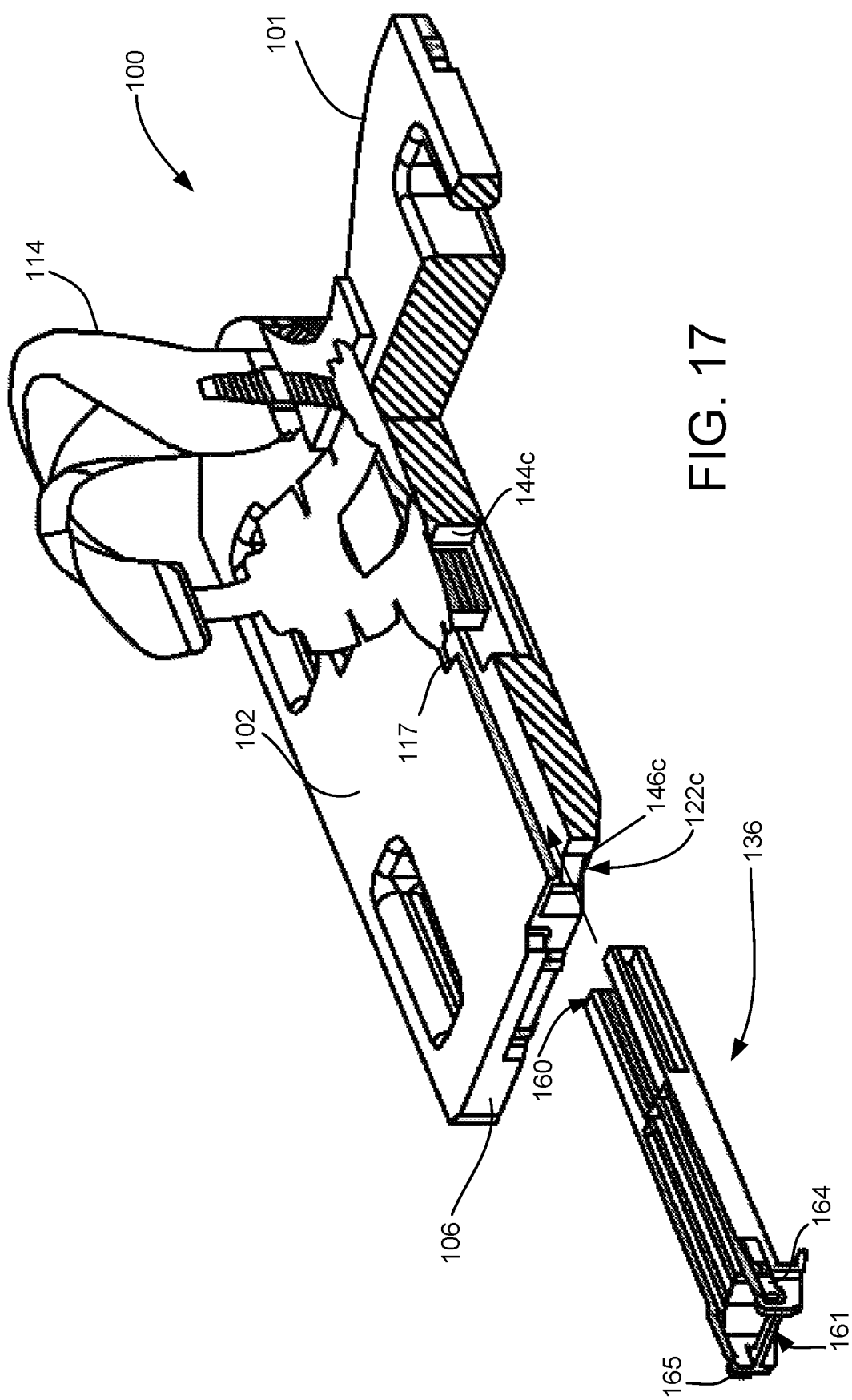
FIG. 17 is a partial perspective view of a section of the spine board illustrating the insertion of and placement of the collar stabilization key in the spine board.

FIG. 17 is a partial perspective view of a section of spine board 100 illustrating the insertion of and placement of collar stabilization key 136 in main body 101 of spine board 100. As illustrated, the leading end 160 of collar stabilization key 136 is inserted into a third longitudinal channel 122c in the direction illustrated by the directional arrows. Third longitudinal channel 122c includes a first end 144c and a second end 146c and is located between first and second longitudinal channels 122a and 122b. Second end 146c intersects with first end 106 of main body 101. Collar stabilization key 136 is slid into third longitudinal channels 122c in the direction illustrated by the directional arrow until leading end 160 reaches first end 144c of channel 122c where post 115 is inserted through an opening 117 in top surface 102 of main body 101. As collar stabilization key 136 reaches its full insertion position, the spring or barbed clips 164 and 165 on trailing end 161 will become compressed and as insertion is completed the spring or barbed clips 164 and 165 will click into position, thereby indexing with main body 101 and holding collar stabilization key 136 in place as well as post 115, which prevents any motion of the patient's neck (either lateral translation and rotation) during transportation. The spring or barbed clips also prevent collar stabilization key 136 from being removed accidentally. Collar stabilization key 136 can be easily removed from main body 101 by grasping spring or barbed clips 163 and 164 and squeezing them toward the center of collar stabilization key 136 while pulling the collar stabilization key 136 from longitudinal channel 122c of main body 101.

Figure 18:
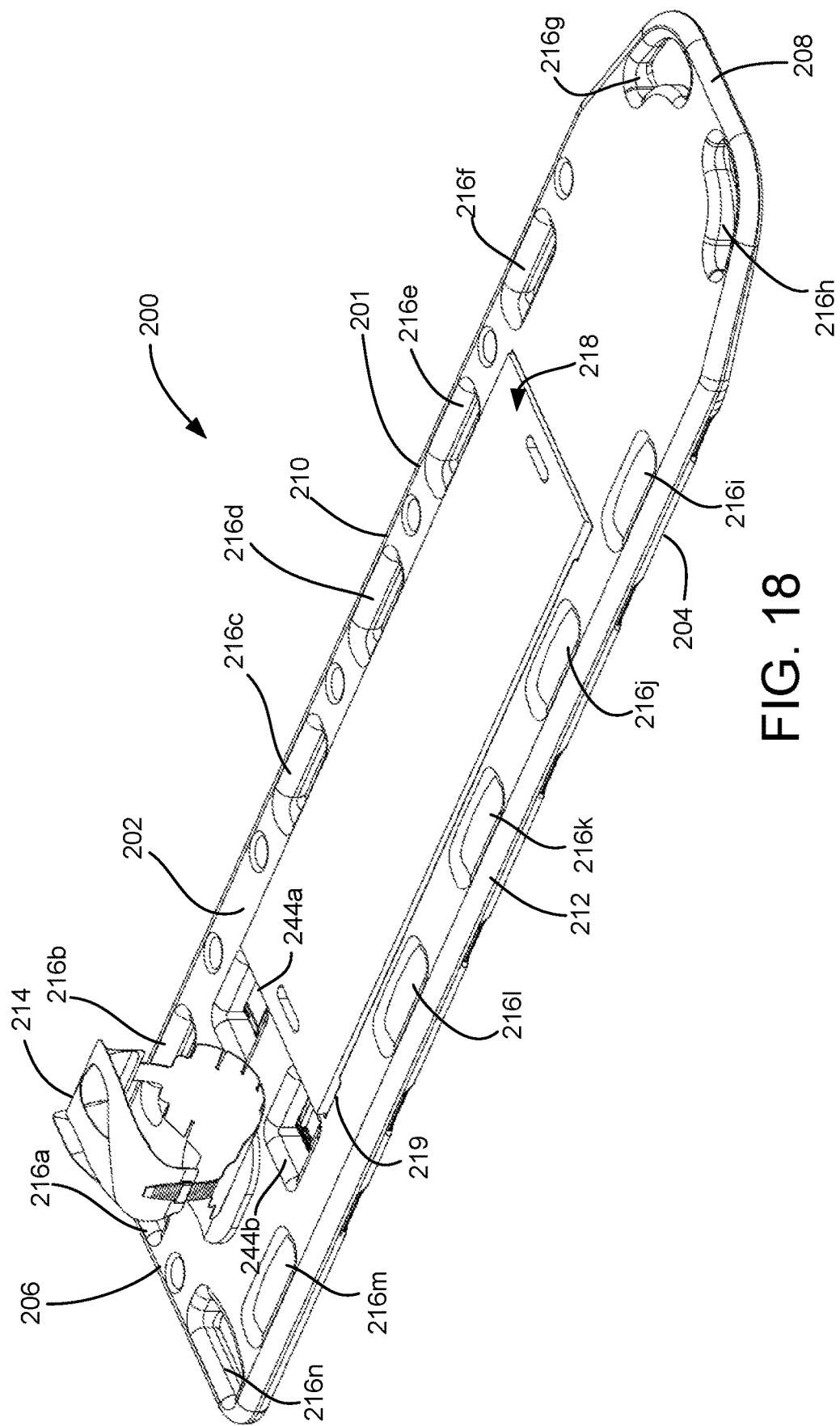
FIG. 18 is a perspective view illustrating a spine board and a cervical collar mounted to the spine board according to another embodiment.
Figure 19:
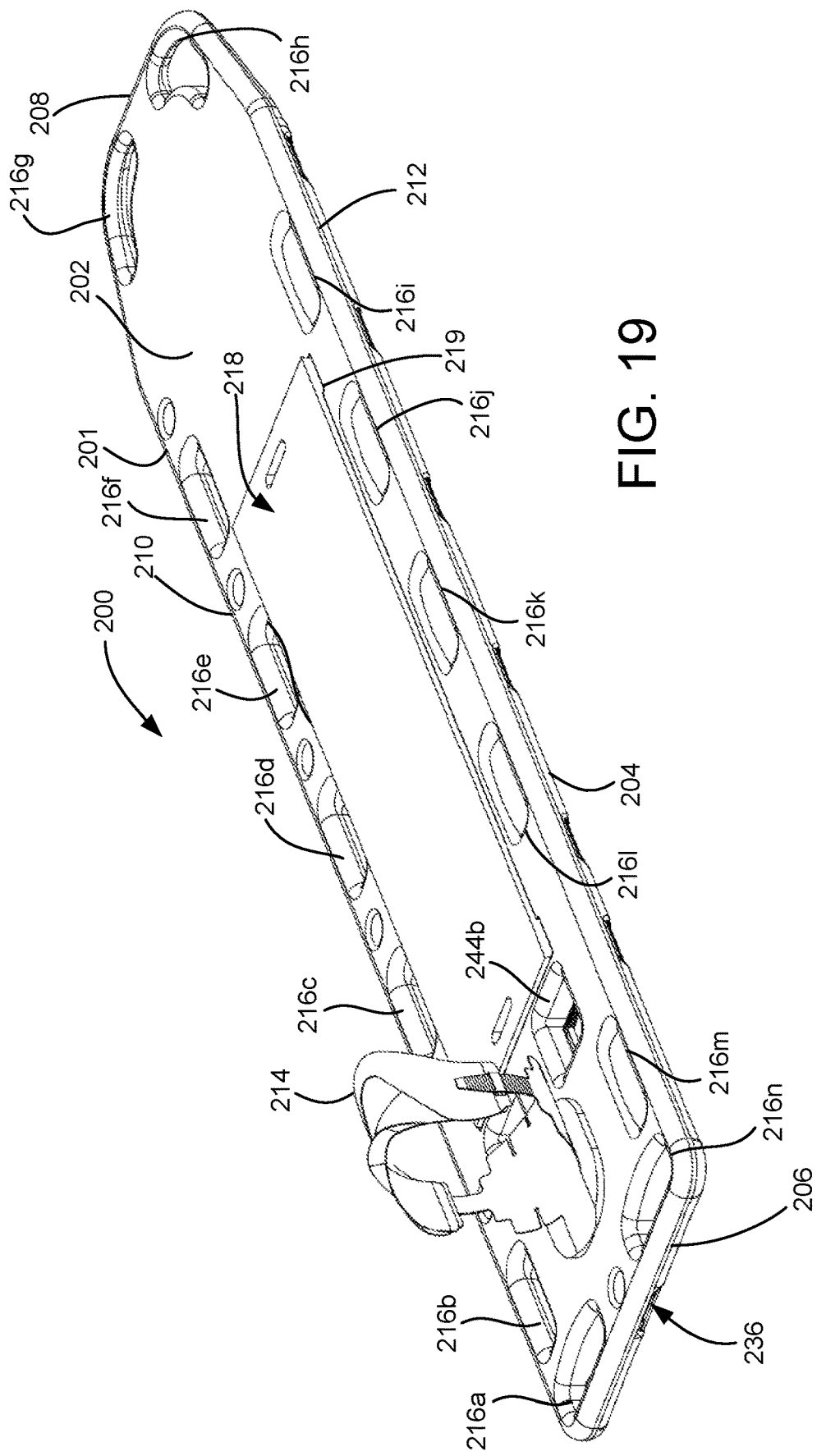
FIG. 19 is another perspective view showing the spine board and the cervical collar illustrated in FIG. 18.
Figure 24:
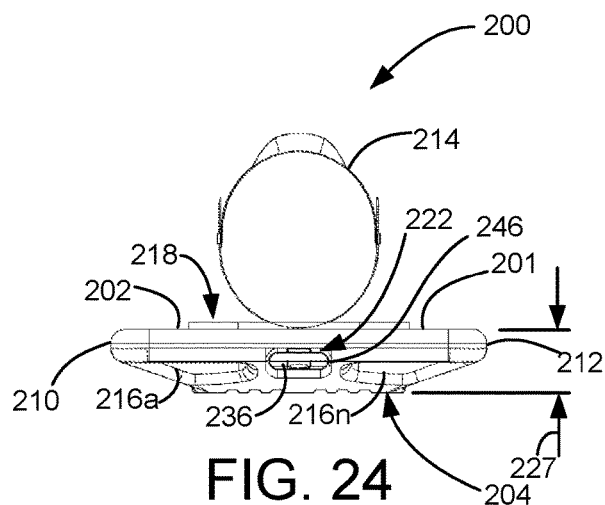
FIG. 24 is a back end view of FIGS. 18 and 19.
Figure 25:
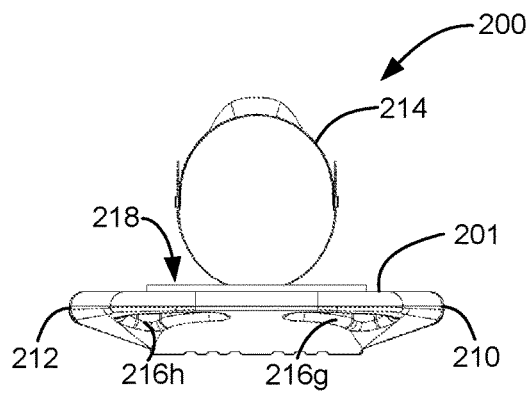
FIG. 25 is a front end view of FIGS. 18 and 19.

FIGS. 18 and 19 are perspective views of another embodiment of a support article or spine board 200. FIGS. 20-25 are a top view, a bottom view, a right side view, a left side view, a back end view and a front end view of spine board 200. Like spine board 100, spine board 200 includes a main body 201 having a top surface 202, an opposing bottom surface 204, a first end 206, an opposing second end 208, a first longitudinal side 210 and an opposing second longitudinal side 212. The distance between top surface 202 and bottom surface 204 defines a thickness 227 (FIG. 24) of main body 201. Bottom surface 204, in the embodiment illustrated in FIGS. 18-25, is not flat, but has longitudinal ridges, which provide increased strength to board 200. The distance between first end 206 and second end 208 defines a length 223 (FIG. 20) of main body 201. The distance between first longitudinal side 210 and second longitudinal side 212 defines a width 225 (FIG. 20) of main body 201. First and second longitudinal sides 210 and 212 connect first and second ends 206 and 208. In one embodiment, spine board 200 is made of a light-weight synthetic material, durable enough to withstand years of use by medical personnel.

Handles 216a-n are spaced apart from each other and are placed in locations adjacent to and along first end 206, second end 208, first longitudinal side 210 and second longitudinal side 212 to allow medical personnel to carry spine board 200. Along the mid-section of main body 201 of board 200, spine board 200 includes a recess 219 having undercut features on either longitudinal side of recess 219 for receiving a comfort pad 218 that protrudes slightly from top surface 202 of main body 201. Spine board 200 also includes an adjustable brace or cervical collar 214 mounted to main body 201 that also protrudes from top surface 202. Cervical collar 214 is fitted around a patient's neck and then fixed to board 200 prior to patient transport to prevent as much movement of the spine as possible. A collar stabilization key 236 (FIGS. 19, 21 and 24) is located internal to main body 201 of board 200 and is used to hold the cervical collar 214 in place and prevent motion of the head and neck in multiple directions. The embodiment of cervical collar 214 and collar stabilization key 236 will be discussed in more detail below.

Figure 26:
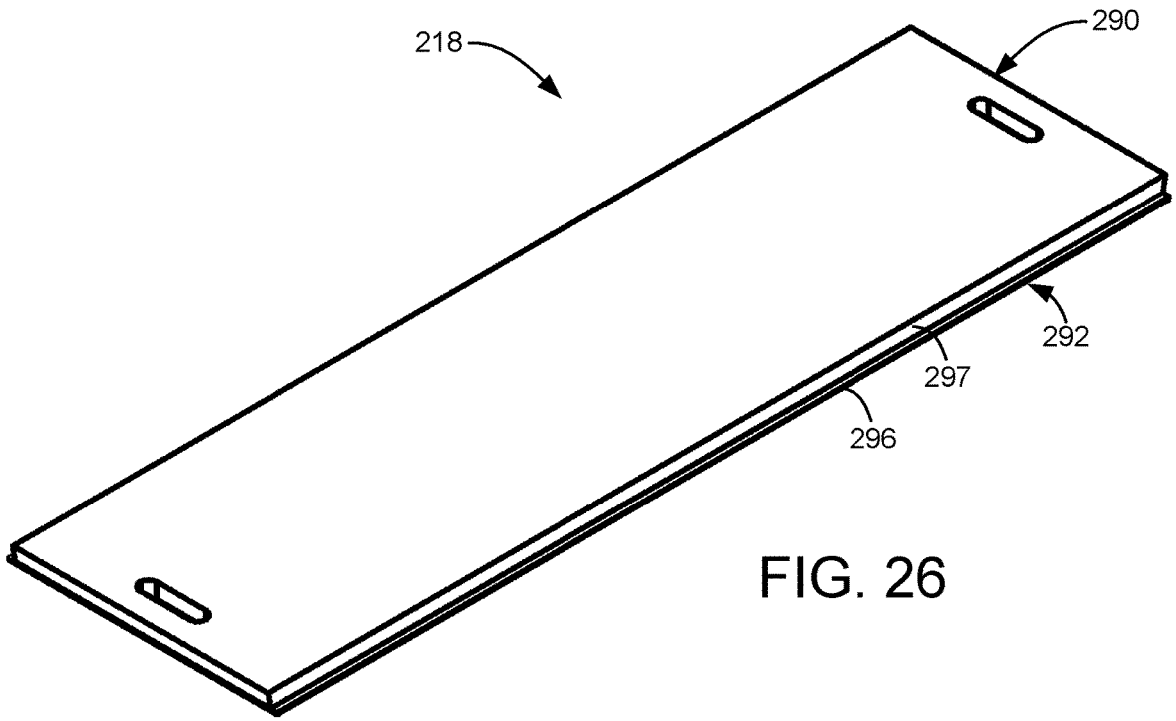
FIG. 26 is a perspective view of a comfort pad that is to be mounted to the spine board illustrated in FIGS. 18-25 according to one embodiment.
Figure 27:
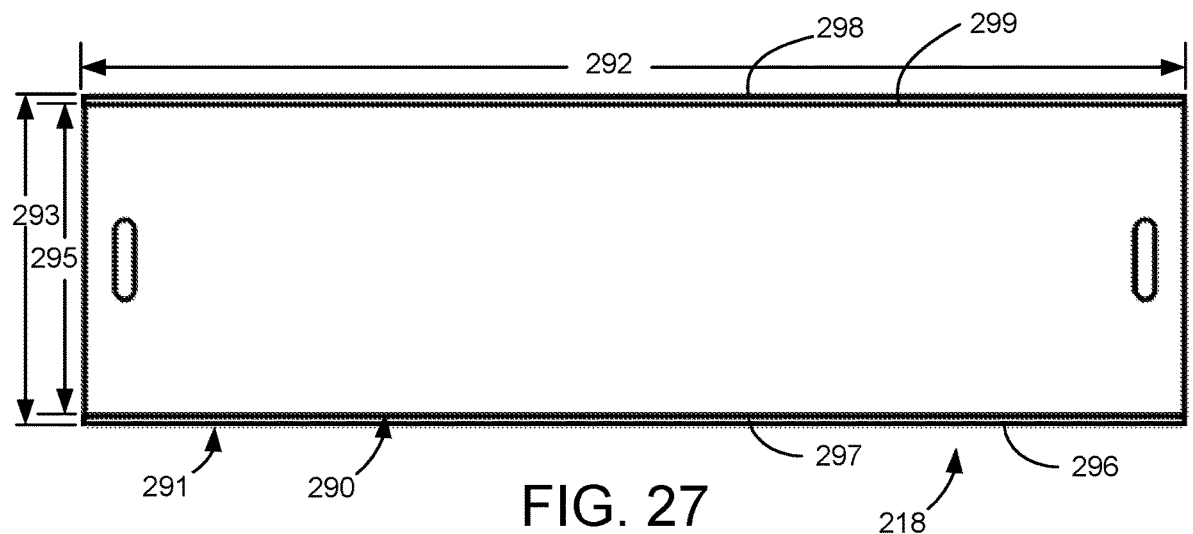
FIG. 27 is a top view of FIG. 26.
Figure 28:
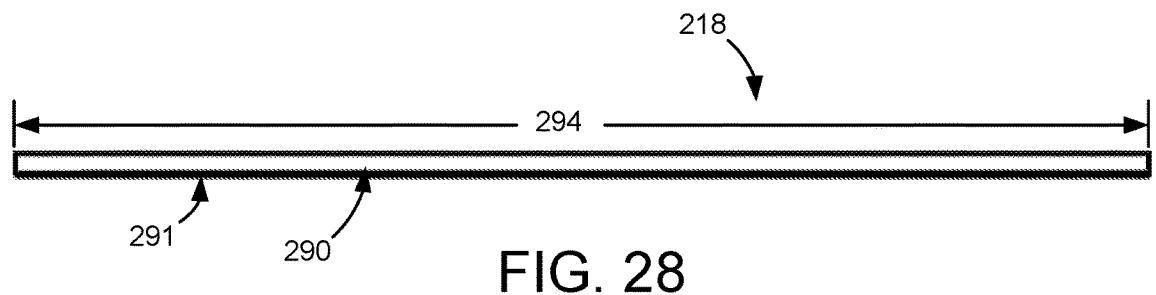
FIG. 28 is a side view of FIG. 26.
Figure 29:
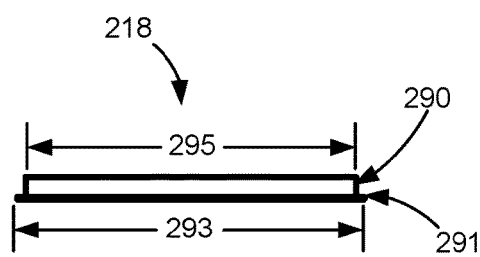
FIG. 29 is an end view of FIG. 26.

FIG. 26 is a top perspective view of comfort pad 218 before it is mounted to spine board 200. FIGS. 27-29 are a top view, a side view and an end view of comfort pad 218. In one embodiment, comfort pad 218 includes a foam body 290 mounted to a backer 291 with, for example, an adhesive. Backer 291 includes a length 292 and a width 293 and foam body 290 includes a length 294 and a width 295. While length 292 of backer 291 and length 294 of foam body 290 are substantially the same, width 293 of backer 291 is greater than width 295 of foam body 290. In particular, backer 291 extends outwardly from either longitudinal side of foam body 290 so that a first longitudinal side 296 of backer 291 is spaced outwardly from a first longitudinal side 297 of foam body 290 and a second longitudinal side 298 of backer 291 is spaced outwardly from a second longitudinal side 299 of foam body 290. Foam body 290 may be constructed of polyethylene foam and backer 291 may be constructed of a corrugated cardboard. In other embodiments, comfort pad 218 may or may not contain chemically activated ice and is capable of reducing the potential for pressure ulcers that a patient might develop. For example, foam body 290 may include a mechanism to allow for ice packs to be placed down its center. However, it is also possible that foam body 290 is a continuous pad with no ice.

To attach comfort pad 218 to spine board 200, one extending section of backer 291 that extends outwardly from one of longitudinal sides 297 or 299 of foam body 290 is inserted first into one of the longitudinal undercut features of recess 219. Then the other extending section of backer 291 that extends outwardly from the other of longitudinal sides 297 or 299 of foam body 290 is inserted into the other of the longitudinal undercut features of recess 219.

Also incorporated into the board are a plurality of channels and a plurality of cartridges that are inserted in the channels and contain straps. The channels exist within main body 201 and are located interior to the outer surfaces of board 200 including between top surface 202 and bottom surface 204 and between first end 206 and second end 208 and between first longitudinal side 210 and second longitudinal side 212. The channels provide openings to receive the cartridges, which contain the straps that secure the patient to the board. The cartridges are single use units that are loaded and stored within the board and provide easy access to the straps when needed for treatment of the patient.

Figure 30:
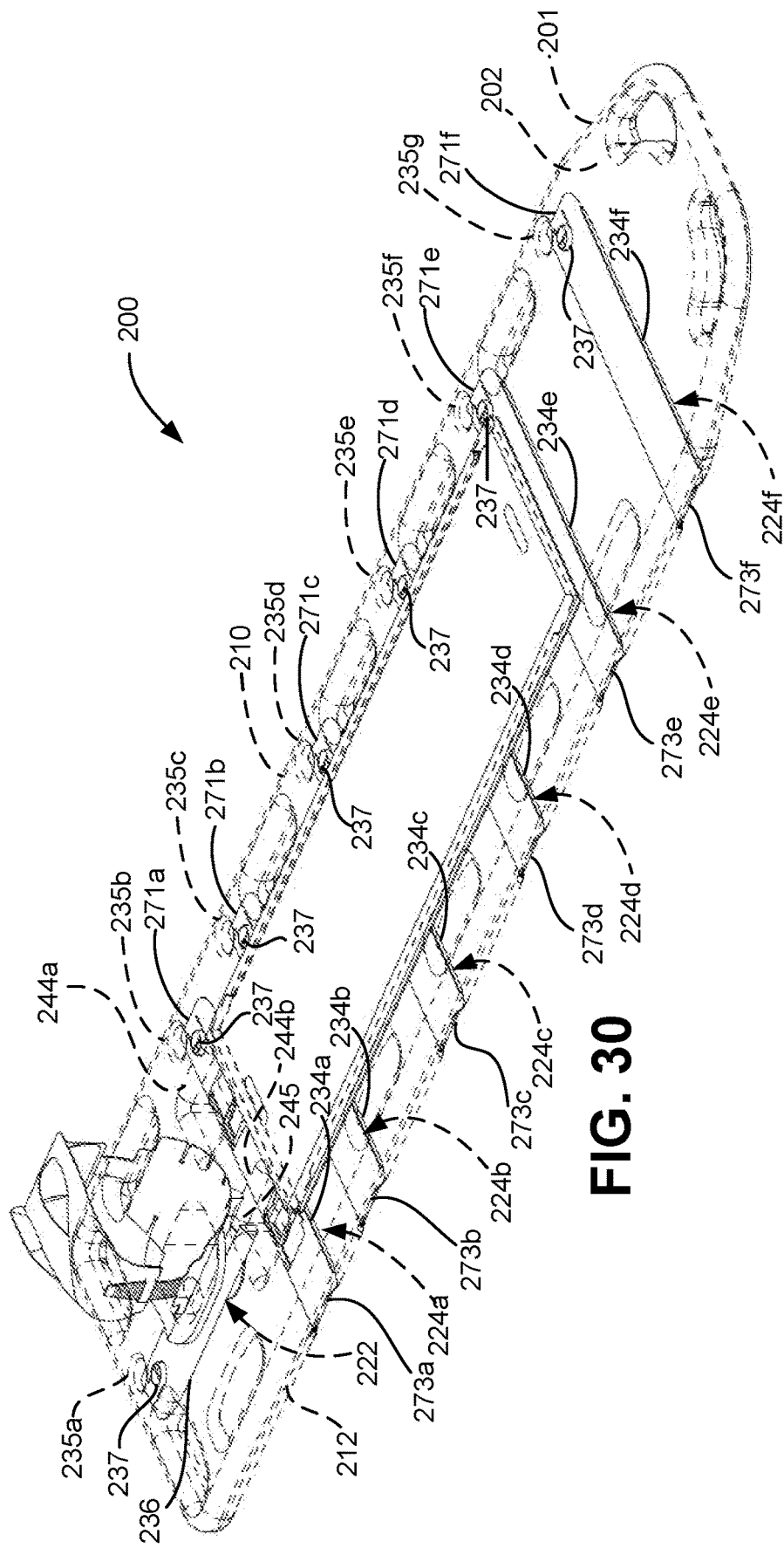
FIG. 30 is the perspective view illustrated in FIG. 18 with the spine board shown in phantom to illustrate other components.
Figure 41:
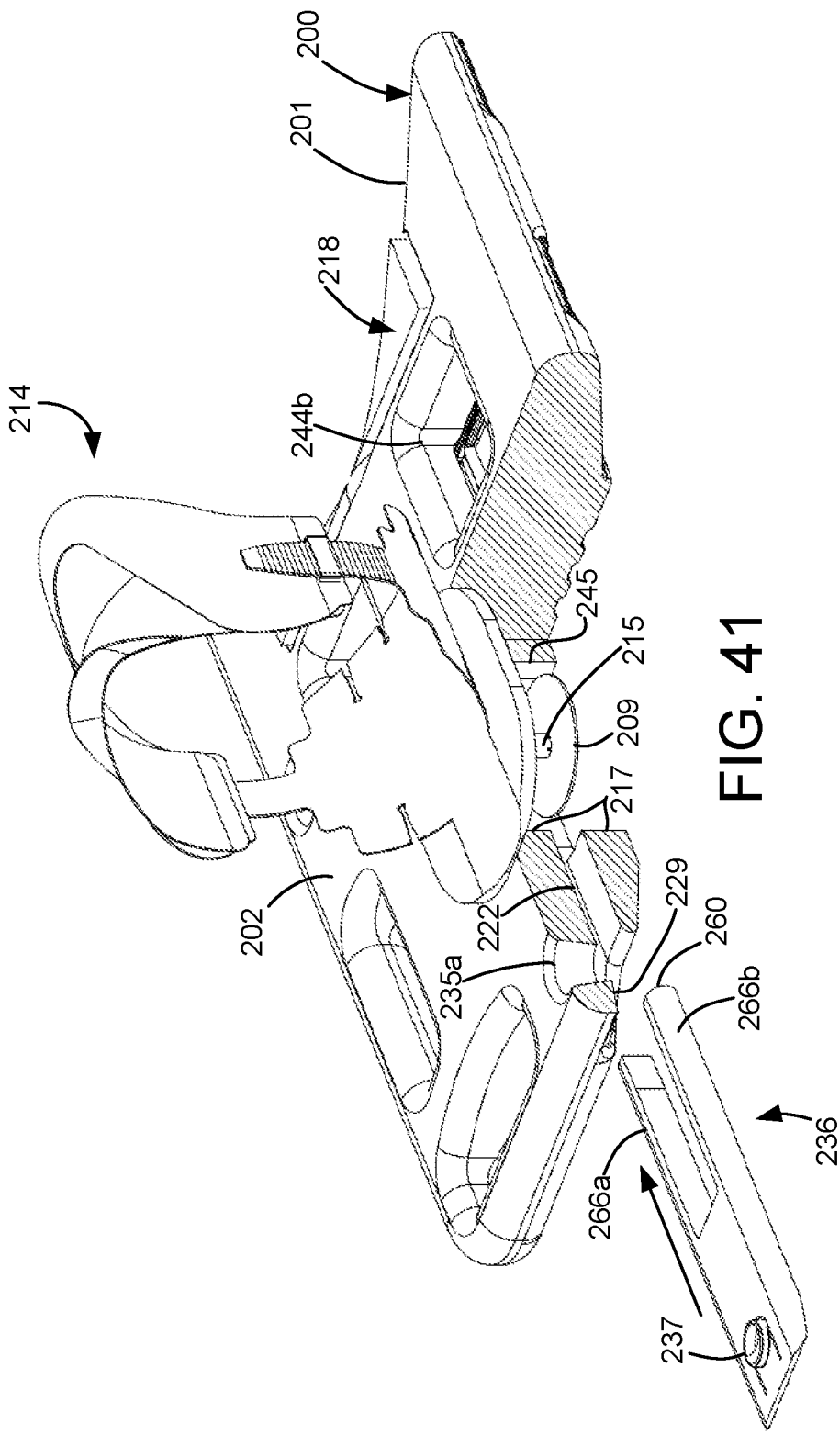
FIG. 41 is a partial perspective view of a section of the spine board of FIGS. 18 and 19 illustrating the insertion of and placement of the collar stabilization key of FIG. 37 in the spine board to secure the cervical collar of FIG. 33.

In one embodiment, there are two different types of channels that exist within main body 201 of board 200—a single longitudinal channel and a plurality of lateral channels. A single longitudinal channel 222 (FIG. 24) extends longitudinally along a portion of length 223 of spine board 200 and is located centrally to the spine board from a first end 246 (FIGS. 24 and 41) to a second end 245 (FIGS. 30 and 41). Longitudinal channel 222 is configured to receive collar stabilization key 236, which will be discussed in detail below. A plurality of lateral channels 224a-f (FIGS. 22 and 23) extend laterally through width 225 of main body 201 from first longitudinal side 210 to second longitudinal side 212.

FIG. 30 is the perspective view of spine board 200 in FIG. 18 with main body 201 shown in phantom to illustrate internal components. Longitudinal channel 222 is located inside main body 201 between top surface 202 and bottom surface 204 and has second end 245, which is closed, and first end 246 (FIG. 24), which is open. Open first end 246 intersects with first end 206 of main body 201 and serves as the insertion opening into channel 222 for collar stabilization key 236.

Lateral channels 224a, 224b, 224c, 224d, 224e and 224f are oriented substantially perpendicular to longitudinal channel 222, but do not intersect longitudinal channel 222 since they are spaced away from longitudinal channel 222. Lateral channels 224a-f are also located inside main body 201 between and spaced apart from top surface 202 and bottom surface 204. Each channel 224a-f has a length that is width 225 of main body 201, are spaced apart from each other along length 223 of main body 201 and have open first ends 226a, 226b, 226c, 226d, 226e and 226f (FIG. 22) that intersect with first longitudinal side 210 and open second ends 228a, 228b, 228c, 228d, 228e and 228f (FIG. 23) that intersect with second longitudinal side 212. Both open first ends 226a-f and open second ends 228a-f serve as exit ends for straps stored in cartridges 234a-f.

As illustrated and as previously discussed, longitudinal channel 222 and lateral channels 224a-f that exist within main body 201 of spine board 200 house and store removable cartridges. The removable cartridges that are housed within lateral channels 224a-f have an oval clamshell shape and contain straps. Longitudinal channel 222 receives collar stabilization key 236, which may be thought of as a cartridge, but has a different shape that will be discussed below. Lateral channels 224a-f receive and house lateral cartridges 234a, 234b, 234c, 234d, 234e and 234f having leading ends 273a-f and trailing ends 271a-f, respectively. Each cartridge 234a-f contains and stores a strap used to secure the patient to main body 201 of board 200. The straps are made with hook and loop material for securing via attachment onto themselves. In particular, first ends of the straps stored in cartridges 234b-f exit through first ends 226b-f and second ends of the straps stored in cartridges 234b-f exit through second ends 228b-f. The straps are configured for wrapping around a patient and securing the patient's body to spine board 100 in a cross-body configuration. It should be pointed out that lateral cartridge 234a contained in lateral channel 224a is slightly different than other lateral cartridges 234b-f. Lateral cartridge 234a contains a shoulder strap and its ends exit from spine board 100 through holes 244a and 244b.

The trailing end of each channel 222, 224a-f includes an aperture 235a-g. Each aperture 235a-g is located either adjacent to first end 206 of spine board 200 or adjacent to first longitudinal side 210 of spine board 200. Each aperture 235a-g extends from the top surface 201 of spine board 200 and intersects with each channel 222, 224a-f. In addition, a locking button 237 is located on the trailing end of each cartridge 234a-f and 236. Each channel 222, 224a-f includes a ramp feature 229 (FIG. 41) located at each of the trailing ends of the channels that allow for locking button 237 to become compressed during insertion. Then, button 237 releases into one of the apertures 235a-g in top surface 201 of spine board 200. Depressing any of buttons 237 allows that particular cartridge 234a-f or 236 to slide out of board 200.

Figure 31:
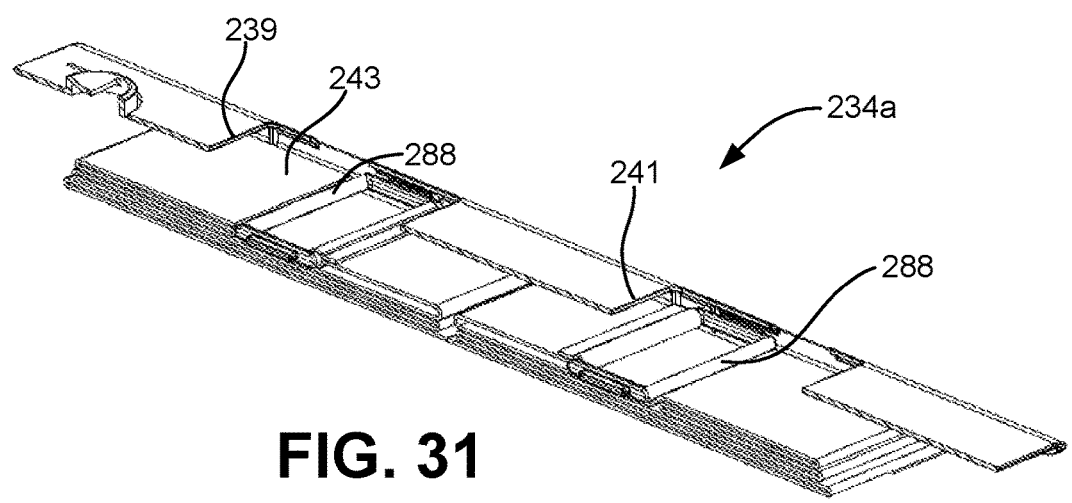
FIG. 31 is a sectional perspective view of an exemplary cartridge.
Figure 32:
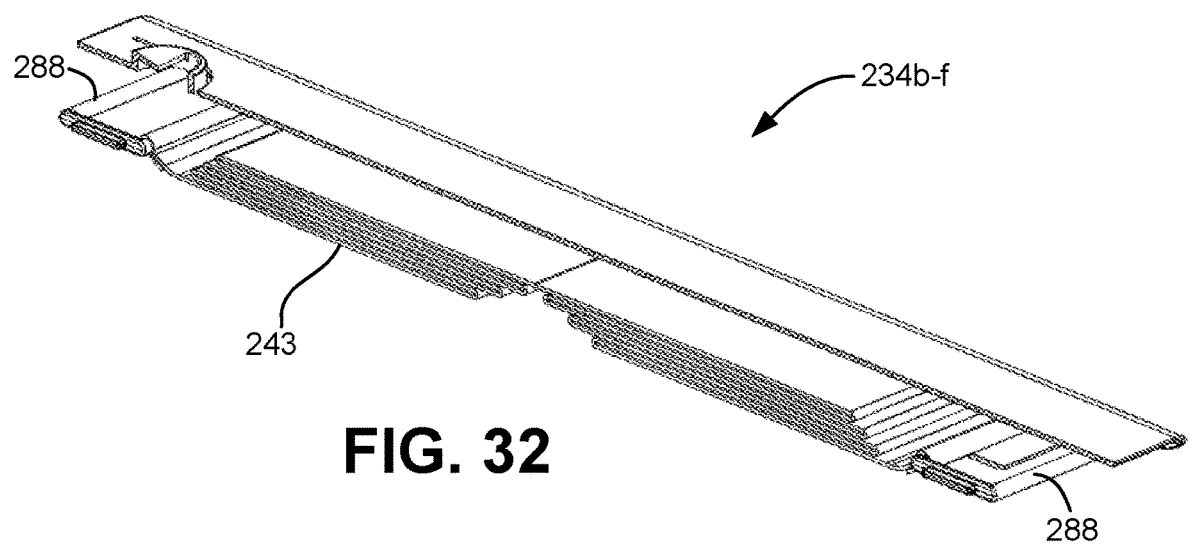
FIG. 32 is a section perspective view of another exemplary cartridge.

Straps stored in lateral cartridges 234a-f are allowed to freely slide within and are positioned in a dual serpentine arrangement of hook and loop strap material (i.e., a dual arrangement of strap material are folded over and onto itself) as are illustrated in the exemplary configurations in FIGS. 31 and 32. In FIG. 31, cartridge 234a is illustrated and in FIG. 32, any of cartridges 234b-f are illustrated. Cartridge 234a includes first top surface opening 239 and second top surface opening 241. Each top surface opening 239 and 241 extends from the top surface of the elongated body to the hollow interior of the hollow elongated body. A first end of the strap that includes finger hook 288 exits through first top surface opening 239 and a second end of the strap that includes finger hook 288 exits through second top surface opening 241. Ends of a shoulder strap 243 are allowed to be accessed from "strap access cavities" or through holes 244a and 244b from lateral cartridge 234a as positioned in lateral channel 224a. Through holes 244a and 244b (FIGS. 18 and 30) are located centrally on board 200 A first end of each lateral strap 132b-f of lateral cartridges 234b-f can exit out a leading end of each lateral cartridge 234b-f and each second end of each lateral strap 132b-f can exit out a trailing end of each lateral cartridge 234b-f. Each end of the dual arrangement of strap material includes a finger hook 288.

As illustrated in FIG. 30, to insert and place lateral cartridges 234a-f in main body 201 of spine board 200, the leading ends 273a-f of lateral cartridges 234a-f are inserted into channels 224a-f, respectively, and are slid from first longitudinal side 210 of main body 201 to second longitudinal side 212 until trailing ends 271a-f reach first longitudinal side 210 and locking buttons 237 release into place into apertures 235b-g.

The straps, made of hook and loop material, are wrapped around the patient and placed on top of themselves or each other to secure the patient's torso, waist and legs to the board. Although unnecessary, it is possible to further thread the straps through the handles by twisting the strap at the handle to allow for hook and loop surfaces to contact each other. All six straps in all six lateral cartridges 234a-f should be utilized to securely fasten the patient to spine board 200.

In regards to lateral cartridge 234a, the straps are brought over the shoulders of the patient, crossed and are attached via its hook and loop material to the lateral straps that were wrapped around the patient. For sanitation purposes, longitudinal cartridge 236 and lateral cartridges 234a-f including the straps that they house are single use and are removed for replacement.

Figure 33:
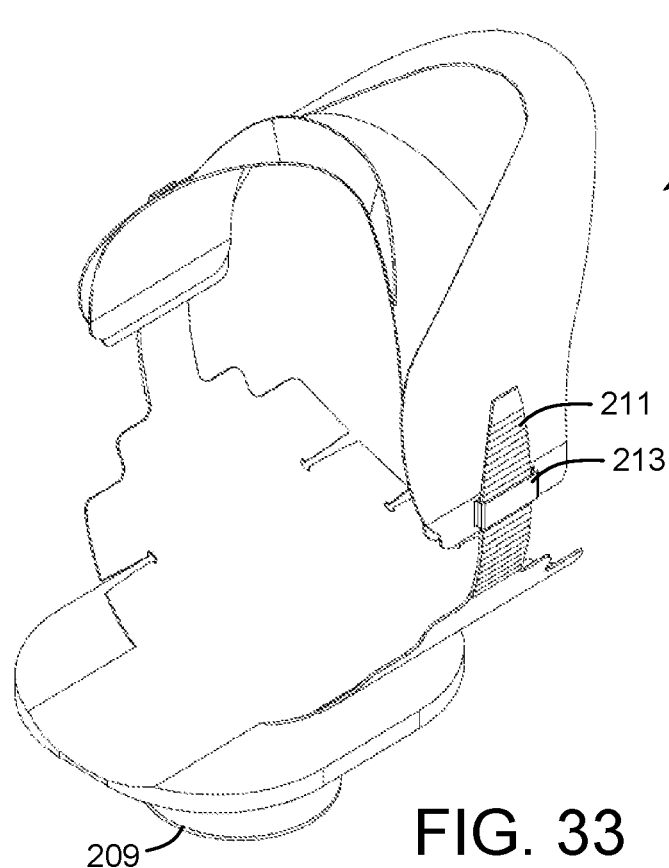
FIG. 33 is a top perspective view of a cervical collar according to another embodiment.
Figure 34:
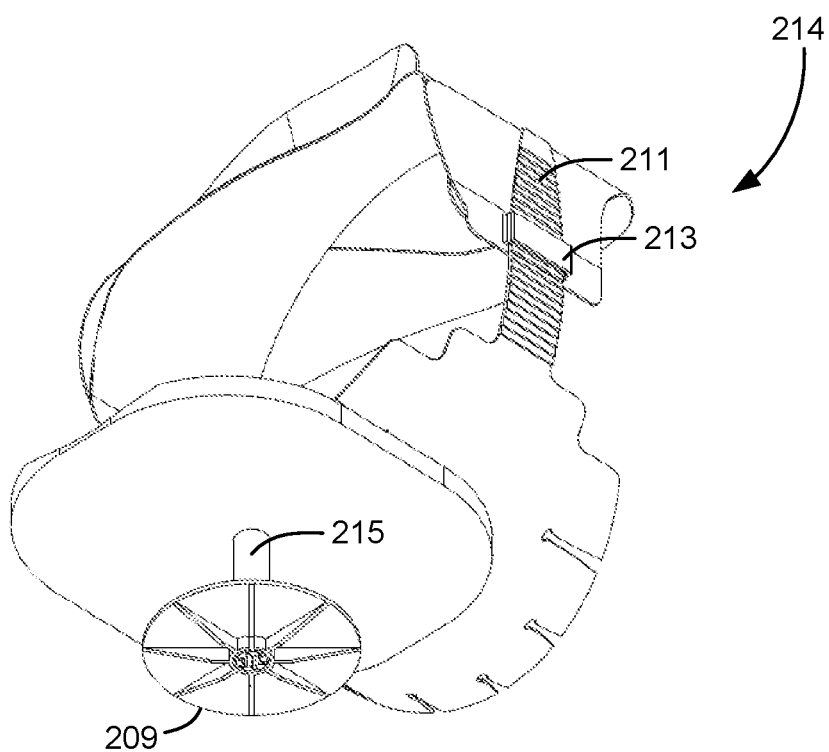
FIG. 34 is a bottom perspective view of the cervical collar of FIG. 33.
Figure 35:
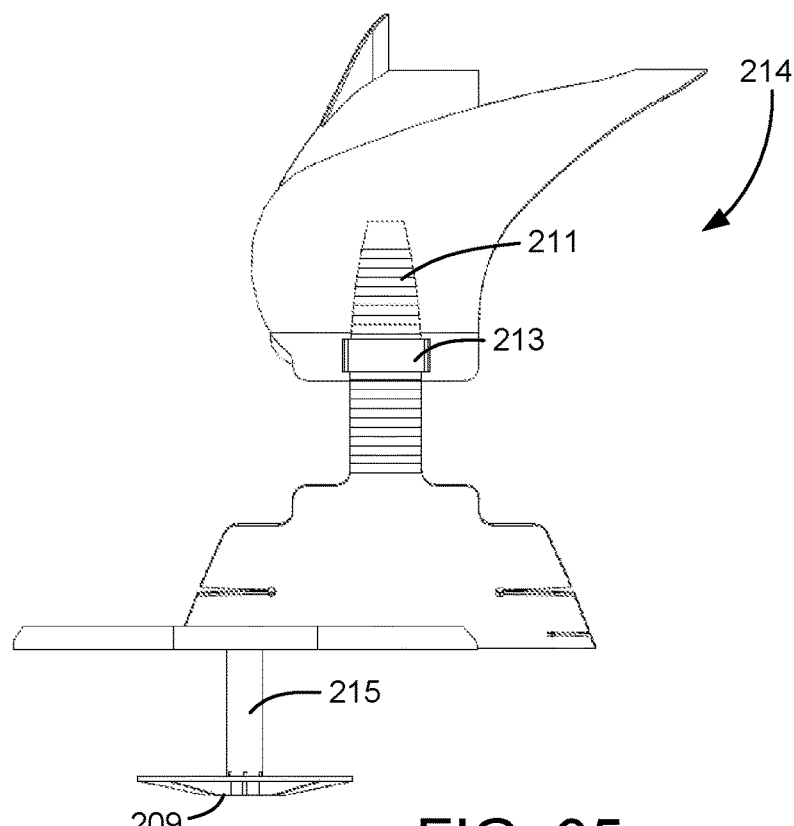
FIG. 35 is a side view of the cervical collar of FIG. 33.
Figure 36:
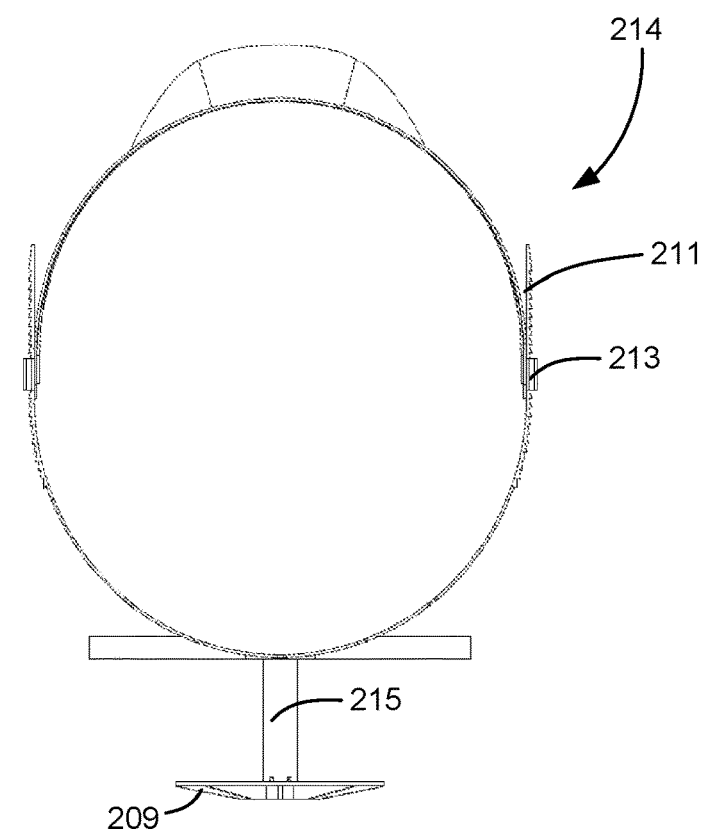
FIG. 36 is an end view of the cervical collar of FIG. 33.

FIGS. 33 and 34 are top perspective and bottom perspective views, respectively, of cervical collar 214. FIG. 35 is a side view of the cervical collar of FIG. 33. FIG. 36 is an end view of the cervical collar of FIG. 33. Cervical collar 214 is composed of different density polyethylene plastic materials based on function. Use of polymer-type materials will be apparent to one of skill in the art. A high density polyethylene provides structural strength when surrounding the cervical portion of the spine as well as provides strength for post 215, which is attached to the back of collar 214. A polyethylene foam provides a pad to the contact areas. An ice pack can also pad the contact areas and will provide a therapeutic cooling effect to the cervical area confined to collar 214 (if activated). Collar 214 stores in a low, flat profile and assumes a three-dimensional configuration when wrapped around the patients neck and secured with a pair of saw tooth straps and corresponding buckles. In addition, collar 214 and post 215 may be radiolucent to allow x-rays to be taken without removal of the patient from the collar or the spine board. In another embodiment, collar 214 can contain phosphors for radiating visible light after being energized so as to be "glow-in-the-dark." Collar 214 is designed to be slid under the arch of the subject's neck. It is secured to the patient using a saw tooth strap 211 and buckle 213 configuration and secured to main body 201 of board 200 using post 215. At a distal end of post 215 is a flange or circular disk 209. Flange 209 has a greater diameter than a diameter of post 215. It should be realized that other ways to secure collar to a patient's neck are possible. In another embodiment, cervical collar 214 has multiple distal contact points including, but not limited to contact points with the bilateral clavicles, bilateral trapezius muscles, the sternum, posterior soft tissues overlying the occiput and anteriorly the mandible and its soft tissue.

Figure 37:
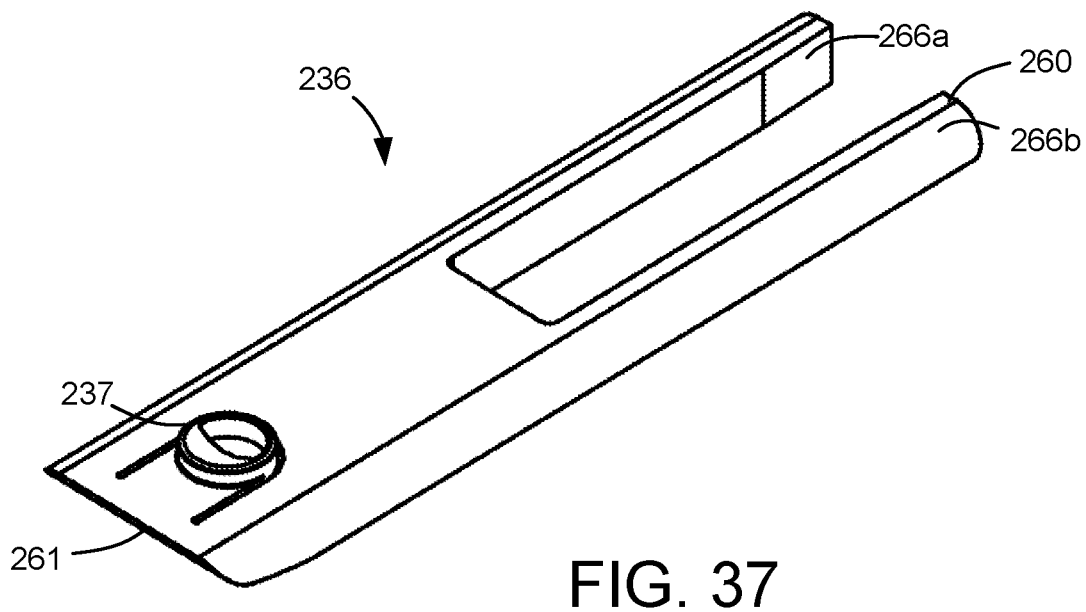
FIG. 37 is a top perspective view of a collar stabilization key for securing the cervical collar of FIG. 33 to the spine board according to another embodiment.
Figure 38:
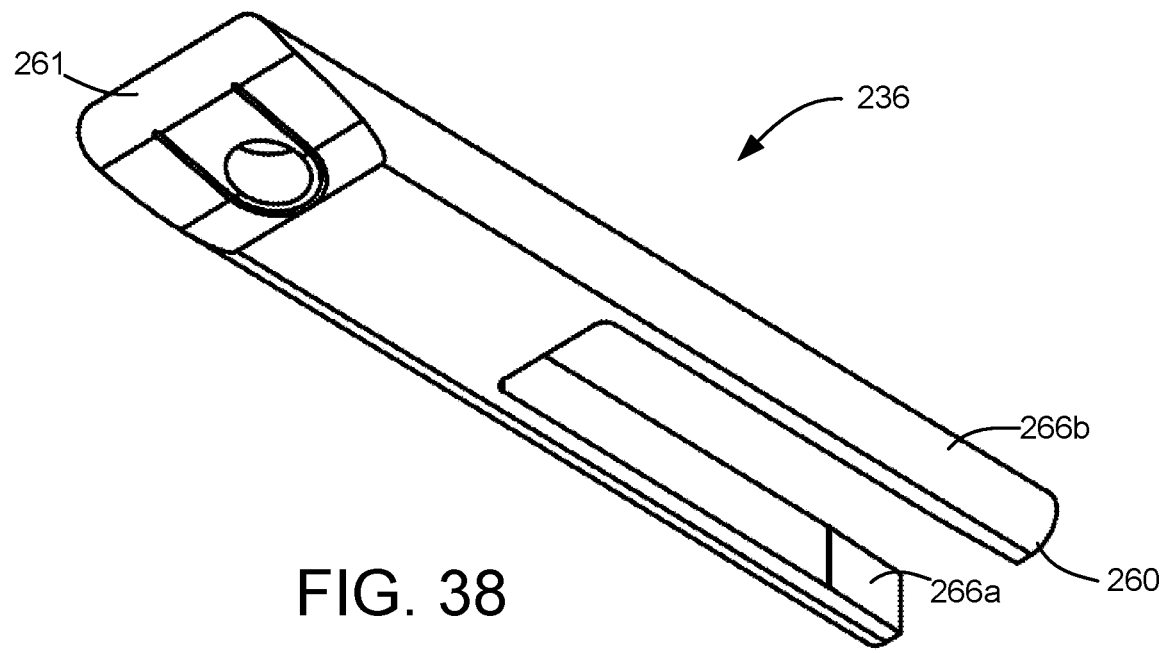
FIG. 38 is a bottom perspective view of FIG. 37.
Figure 39:
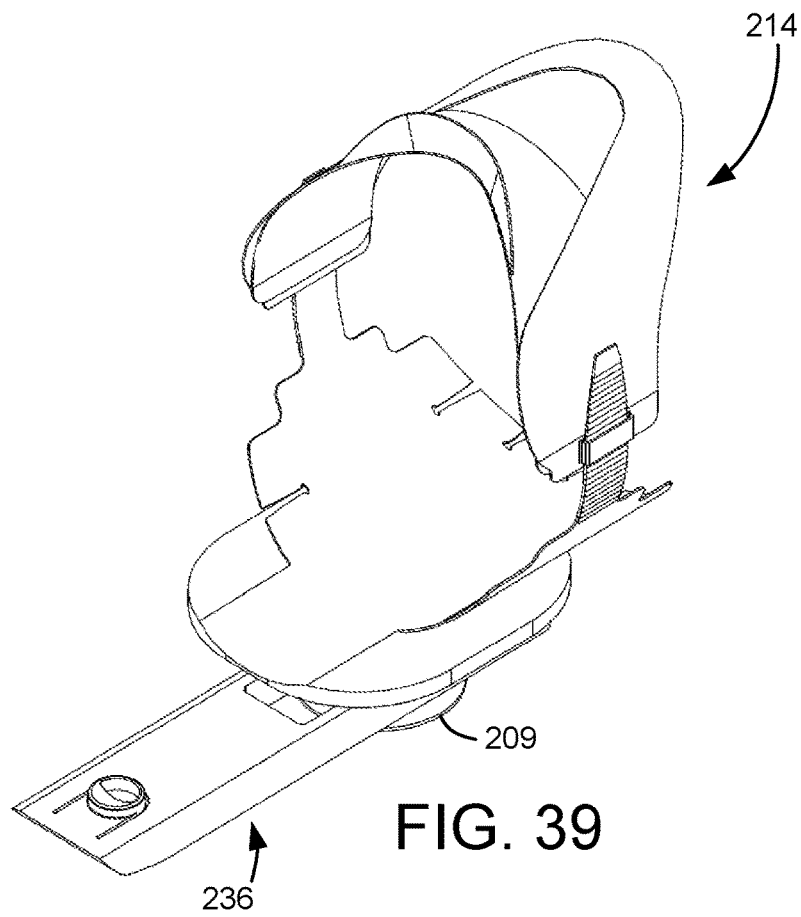
FIG. 39 is a top perspective view of the collar stabilization key of FIG. 37 engaged with the cervical collar of FIG. 33.
Figure 40:
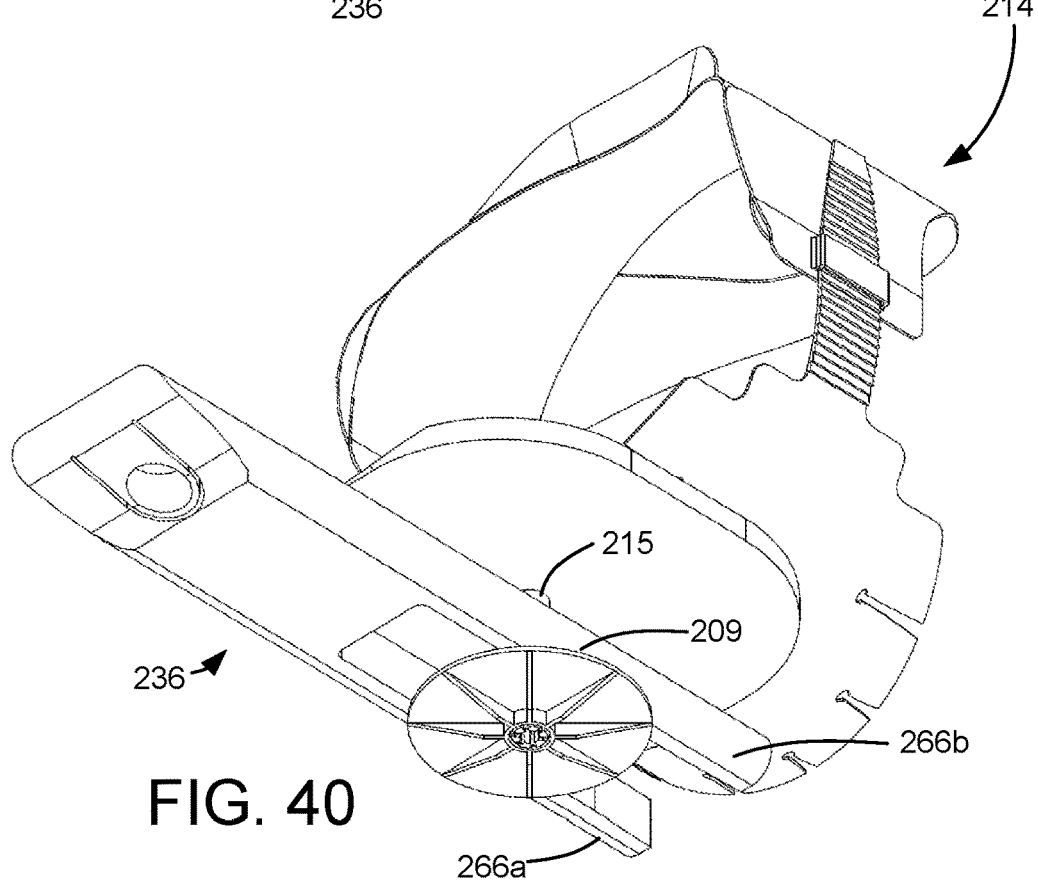
FIG. 40 is a bottom perspective view of FIG. 37.

Post 215 and therefore flange 209 of cervical collar 214 can be inserted into an opening 217 (FIG. 21) in main body 201 of board 200 and locked into place with collar stabilization key 236. FIGS. 37 and 38 are top and bottom perspective views, respectively, of collar stabilization key 236. Collar stabilization key 236 includes a leading end 260 and a trailing end 261. Trailing end 261 includes button 237 (like the other cartridges) for releasing into aperture 235a so that when collar stabilization key 236 is inserted into main body 201 of board 200, collar stabilization key 236 is engaged with main body 201 of board 200. Extending from leading end 260 and less than halfway to trailing end 261 is are a pair of forks 266a and 266b having interior facing sides. Upon placing post 215 and disk 209 through opening 217 in board 200, key 236 is slid into channel 222 and forks 266a and 266b are configured to capture post 215 between the bottom of the body of the collar and flange 209 to secure collar 214 in place. Such engagement is illustrated in the top and bottom perspective view illustrated in FIGS. 39 and 40. The space between the forks 266a and 266b of key 236 along with a small diameter post allows for latitude in positioning the patient's head on board 200.

FIG. 41 is a partial perspective view of a section of spine board 200 illustrating the insertion of and placement of collar stabilization key 236 in main body 201 of spine board 200. As illustrated, the leading end 260 of collar stabilization key 236 is inserted into channel 222 in the direction illustrated by the directional arrow until leading end 260 reaches first end 245 of channel 222 and forks 266a and 266b pass and engage with post 215, which is inserted through an opening 217 in main body 201. As collar stabilization key 236 reaches its full insertion position, button 237 will become compressed and as insertion is completed the button will release or click into position or into aperture 235a, thereby holding collar stabilization key 236 in place as well as post 215, which prevents any motion of the patient's neck (either lateral translation and rotation) during transportation. Collar stabilization key 236 can be easily removed from main body 201 by depressing button 237 and pulling collar stabilization key 236 out of channel 222.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A removable cartridge system comprising:
   a spine board;
   a receiving channel in the spine board;
   a removable cartridge removably located in the receiving channel and comprising:
      hollow elongated body having a leading end, a trailing end, a top surface and a bottom surface, wherein the leading end is configured to be inserted into the receiving channel before the trailing end; and
      a button on the elongated body and positioned proximate the trailing end of the elongated body; and
   at least one safety strap housed in the hollow elongated body of the removable cartridge;
   wherein the removable cartridge is configured such that after the removable cartridge is inserted into the receiving channel, the button is removably inserted into an opening in the spine board that intersects with the receiving channel so as to lock the removable cartridge in the receiving channel.

2. The removable cartridge system of claim 1, wherein the at least one safety strap comprises hook and loop material.

3. The removable cartridge system of claim 1, wherein the hollow elongated body comprises two top surface openings that extend from the top surface of the elongated body to the hollow interior of the hollow elongated body, wherein a first end of the at least one strap exits through one of the two openings and a second end of the least one strap exits through the other of the two openings.

4. The removable cartridge system of claim 1, wherein the hollow elongated body of the cartridge comprises a leading end opening and a trailing end opening, the leading end opening extending from the leading end to the hollow interior of the hollow elongated body and the trailing end opening extending from the trailing end to the hollow interior of the hollow elongated body, wherein a first end of the at least one strap exits through the leading end opening and a second end of the at least one strap exits through the trailing end opening.

5. A removable cartridge system comprising:
   a spine board;
   a receiving channel in the spine board;

a removable cartridge removably located in the receiving channel and comprising:
  an elongated hollow body having an outer surface including a leading end, a trailing end, a top surface and a bottom surface, wherein the leading end is configured to be inserted into the receiving channel before the trailing end and the trailing end is configured to be removed from the receiving channel before the leading end;
  at least two openings that extend from the outer surface of the elongated hollow body to a hollow interior of the elongated hollow body; and
  at least one safety strap housed in the elongated hollow body of the removable cartridge and having a first end and a second end, wherein the first end of the at least one strap exits through one of the two openings and the second end of the at least one strap exits through the other of the two openings.

6. The removable cartridge system of claim 5, wherein the at least two openings comprise a first top surface opening that extends from the top surface to the hollow interior of the elongated hollow body and a second top surface opening that extends from the top surface to the hollow interior of the elongated hollow body, wherein the first end of the at least one strap exits through the first top surface opening and the second end of the least one strap exits through the second top surface opening.

7. The removable cartridge system of claim 5, wherein the at least two openings comprise a leading end opening and a trailing end opening, the leading end opening extending from the leading end to the hollow interior of the elongated hollow body and the trailing end opening extending from the trailing end to the hollow interior of the elongated hollow body, wherein the first end of the at least one strap exits through the leading end opening and the second end of the at least one strap exits through the trailing end opening.

8. The removable cartridge system of claim 5, wherein the at least one safety strap comprises hook and loop material.

9. The removable cartridge system of claim 5, further comprising a button on the elongated hollow body and positioned proximate the trailing end of the elongated hollow body.

10. The removable cartridge system of claim 9, wherein after the cartridge is inserted into the receiving channel, the button is inserted into an opening that intersects with the receiving channel so as to lock the cartridge in the channel.

11. A removable cartridge system comprising:
  a spine board;
  a receiving channel in the spine board;
  a removable cartridge removably located in the receiving channel and including an elongated hollow body having a leading end, a trailing end, a top surface, a bottom surface, a first side and an opposing second side, wherein the leading end is configured to be inserted into the receiving channel before the trailing end;
  a leading end opening extending from the leading end to a hollow interior of the elongated hollow body;
  a trailing end opening extending from the trailing end to the hollow interior of the elongated hollow body; and
  at least one safety strap held in the hollow interior of the elongated hollow and having a first end and a second end, wherein a first end of the at least one strap is configured to exit through the leading end opening and the second end of the at least one strap is configured to exit through the trailing end opening.

12. The removable cartridge system of claim 11, further comprising a button on the elongated hollow body positioned proximate the trailing end of the elongated body.

13. The removable cartridge system of claim 12, wherein the button is configured to be inserted into an opening that intersects with the receiving channel after the removable cartridge is removably located in the receiving channel so as to lock the removable cartridge in the channel.

14. The removable cartridge system of claim 11, wherein the at least one safety strap comprises hook and loop material.

15. The removable cartridge system of claim 11, wherein the first end of the at least one safety strap comprises a first finger hook and the second end of the at least one safety strap comprises a second finger hook.

* * * * *